(12) United States Patent
Ornstein et al.

(10) Patent No.: US 11,666,068 B2
(45) Date of Patent: Jun. 6, 2023

(54) SWEET POTATO LEAF PROTEIN CONCENTRATES AND METHODS FOR OBTAINING THE SAME

(71) Applicant: Leafpro, LLC, Wilson, NC (US)

(72) Inventors: Jason M. Ornstein, London (GB); Emily Lanier, New Hill, NC (US); Tyre Lanier, New Hill, NC (US)

(73) Assignee: LEAFPRO, LLC, Wilson, NC (US)

( * ) Notice: Subject to any disclaimer, the term of this patent is extended or adjusted under 35 U.S.C. 154(b) by 107 days.

(21) Appl. No.: 17/058,447

(22) PCT Filed: May 29, 2019

(86) PCT No.: PCT/US2019/034233
§ 371 (c)(1),
(2) Date: Nov. 24, 2020

(87) PCT Pub. No.: WO2019/231938
PCT Pub. Date: Dec. 5, 2019

(65) Prior Publication Data
US 2021/0378259 A1   Dec. 9, 2021

Related U.S. Application Data

(60) Provisional application No. 62/678,166, filed on May 30, 2018.

(51) Int. Cl.
*A23J 1/00* (2006.01)
*A23L 33/105* (2016.01)
(Continued)

(52) U.S. Cl.
CPC ............... *A23J 1/007* (2013.01); *A23J 3/14* (2013.01); *A23L 2/66* (2013.01); *A23L 19/105* (2016.08);
(Continued)

(58) Field of Classification Search
CPC .......... A23J 1/007; A23J 3/14; A23L 33/105; A23L 19/105; A23L 33/185; A23L 2/66; C07K 1/145; C07K 14/415
(Continued)

(56) References Cited

U.S. PATENT DOCUMENTS 4,268,632 A   5/1981   Wildman et al.
4,289,147 A   9/1981   Wildman et al.
(Continued)

FOREIGN PATENT DOCUMENTS

CN   103284277 A   9/2013
CN   106072607 A   11/2016

OTHER PUBLICATIONS

Walter, W. M. et al. J. Agric. Food Chem. 26-1222-1226 (Year: 1978).*
(Continued)

*Primary Examiner* — Hamid R Badr
(74) *Attorney, Agent, or Firm* — Myers Bigel, P.A.

(57) ABSTRACT

Described herein is a concentrated sweet potato leaf protein in dried form, along with methods for producing it. The concentrated leaf protein has a protein content of greater than 21% by weight, and can have other beneficial components such as polyphenols. The concentrated leaf proteins are suitable for use in food and beverages, as protein supplementation, or as agents for gelling, foaming, and whipping.

17 Claims, 4 Drawing Sheets

(51) Int. Cl.
| | |
|---|---|
| *A23L 19/10* | (2016.01) |
| *A23L 33/185* | (2016.01) |
| *A23J 3/14* | (2006.01) |
| *A23L 2/66* | (2006.01) |
| *C07K 1/14* | (2006.01) |
| *C07K 14/415* | (2006.01) |

(52) U.S. Cl.
CPC ........... *A23L 33/105* (2016.08); *A23L 33/185* (2016.08); *C07K 1/145* (2013.01); *C07K 14/415* (2013.01); *A23V 2002/00* (2013.01)

(58) Field of Classification Search
USPC .......................................................... 426/52
See application file for complete search history.

(56) References Cited

U.S. PATENT DOCUMENTS

| | | | |
|---|---|---|---|
| 4,333,871 | A | 6/1982 | De |
| 4,334,024 | A | 6/1982 | Johal |
| 4,340,676 | A | 7/1982 | Bourque |
| 4,347,324 | A | 8/1982 | Wildman et al. |
| 4,400,471 | A | 8/1983 | Johal |
| 4,588,691 | A | 5/1986 | Johal |
| 4,666,855 | A | 5/1987 | Yang et al. |
| 5,369,023 | A | 11/1994 | Nakatani et al. |
| 7,034,128 | B2 | 4/2006 | Turpen et al. |
| 9,321,806 | B2 | 4/2016 | Lo et al. |
| 9,458,422 | B2 | 10/2016 | Lo et al. |
| 9,629,888 | B2 | 4/2017 | Lo et al. |
| 2015/0335043 | A1 | 11/2015 | De Jong et al. |
| 2017/0238590 | A1 | 8/2017 | Bansal-Mutalik et al. |

OTHER PUBLICATIONS

Zhang, C. et al. Food Bioproducts Process. 100: 92-101 (Year: 2016).*
Park, J. S. et al. J. Food Chem. Nanotechnol. 1: 1-12 (Year: 2015).*
International Search Report dated Sep. 20, 2019 for International Application No. PCT/US2019/034233, 10 pages.
International Preliminary Report on Patentability dated Dec. 1, 2020 for International Application No. PCT/US2019/034233, 7 pages.
Ghaly et al., "Extraction of Protein from Common Plant Leaves for Use as Human Food," American Journal of Applied Sciences. 2010, 7, 331-342. (https://www researchgate net/profile/F ahad_Alkoaik/publication/46179128 _Extraction_of_Protei n from Common Plant Leaves for Use as Human Food/links/00463535f86409ab10000000/Extraction-of-Protein-from-Common-Plant-=-Leaves-for-Use-as-Human-Food.pdf).
Park et al., "Chlorogenic Acid Profiles and Antioxidant Potentials of 17 Sweet Potato Varieties Cultivated in Korea: Impact of Extraction Condition and Classification by Hierarchical Clusterin Analysis," J Food Chm. & Nanotech. 2015, 1, 1, 3-12; Abstract, Introduction, (https://pdfs.semanticscholar.org/744d/1a8ac062738f4c092c5f0984dd103052736d.pdf).
Walter, Jr. et al., "Laboratory Preparation of a Protein-Xanthophyll Concentrate from Sweet Potato Leaves," J. Agric. Food Chem.1978, 26, 5, 1222-1226; Abstract, Experimental Section, Results and Discussion; (https://fbns.ncsu.edu/USDAARS/Acrobatpubs/S31-60/S36.pdf).
Wikipedia. 'Lutein' Wikipedia, Wikimedia Foundation, May 14, 2018, p. 1-8. (www.wikipedia.org/wiki/Lutein.).
An et al. "Effect of Harvesting Interval and Defoliation on Yield and Chemical Composition of Leaves, Stems and Tubers of Sweet Potato (*Ipomoea batatas* L. (Lam.)) Plant Parts" Field Crops Research, 82(1):49-58 (2003).
Baldasso et al. "Concentration and purification of whey proteins by ultrafiltration" Desalination, 278:381-386 (2001).
Bals et al. "Economic comparison of multiple techniques for recovering leaf protein in biomass processing" Biotechnology & Bioengineering 108(3):530-537 (2015).
Barbeau et al. "Ribulose bisphosphate carboxylase/oxygenase (rubisco) from green leaves—potential as a food protein" Food Reviews International, 4(1):93-127 (1988).
Batal et al. "Protein Dispersability Index as an Indicator of Adequately Processed Soybean Meal" Poultry Science, 79 (11):1592-1596 (2000).
Bradford, Marion M. "A Rapid and Sensitive Method for the Quantitation of Microgram Quantities of Protein Utilizing the Principle of Protein-Dye Binding" Analytical Biochemistry, 72:248-254 (1976).
Buyel et al. "Extraction and downstream processing of plant-derived recombinant proteins" Biotechnology Advances, 33(6): 902-913(2015).
Eakin et al. "Alfalfa protein fractionation by ultrafiltration" Journal of Food Science, 43:544-547 (1978).
Edwards et al. "Pilot Plant Production of an Edible White Fraction Leaf Protein Concentrate from Alfalfa" Journal of Agricultural and Food Chemistry, 23(4):620-626 (1975).
Fantozzi et al. "Protein extraction from tobacco leaves—technological, nutritional and agronomical aspects" Plant Foods for Human Nutrition, 32:351-368 (1983).
Fu et al. "Antioxidant activities and polyphenols of sweet potato (*Ipomoea batatas* L.) leaves extracted with solvents of various polarities" Food Bioscience, 15:11-18 (2016).
Lamsal et al. "Separation of protein fractions in alfalfa juice: effects of some pre-treatment methods" Transactions of the ASAE, 46(3):715-720 (2003).
Lo et al. "Recovery of nicotine-free proteins from tobacco leaves using phosphate buffer system under controlled conditions" Bioresource Technology, 101:2034-2042 (2010).
Martin et al. "Comparison of the Functional Properties of RuBisCO Protein Isolate Extracted from Sugar Beet Leaves with Commercial Whey Protein and Soy Protein Isolates" Journal of the Science of Food and Agriculture, 99 (4):1568-1576 (2018).
Sun et al. "Sweet potato (*Ipomoea batatas* L.) leaves as nutritional and functional foods" Food Chemistry, 156:380-389 (2014).
Teng et al. "Extraction, identification and characterization of the water-insoluble proteins from tobacco biomass" Journal of the Science of Food and Agriculture, 92(7):1368-1374 (2011).
Tenorio et al. "Understanding Leaf Membrane Protein Extraction" Food Chemistry, 217:234-243 (2017).
Walter et al. "Laboratory Preparation of a Protein-Xanthophyll Concentrate from Sweet Potato Leaves" Journal of Agricultural and Food Chemistry, 26(5):1222-1226 (1978).
Wildman, S. "An Alternate Use for Tobacco Agriculture: Proteins for Food Plus a Safer Smoking Material" Plants: the potentials for extracting protein, medicines, and other useful chemicals: workshop proceedings, pp. 63-77 (1983).
Zhang et al. "How Does Alkali Aid Protein Extraction in Green Tea Leaf Residue: A Basis for Integrated Biorefinery of Leaves" PLoS ONE, 10(7):e0133046 (2015).

* cited by examiner

SWEET POTATO LEAF PROTEIN CONCENTRATES AND METHODS FOR OBTAINING THE SAME

This application is a National Stage 3.71 application claiming the benefit of International Application No. PCT/US2019/034233, filed May 29, 2019, which claims priority from U.S. provisional application 62/678,166, filed May 30, 2018. The entire contents of that provisional are incorporated herein by reference.

FIELD OF THE INVENTION

The invention of this application relates to novel compositions derived from leaves of sweet potatoes, which include high concentrations or isolates of protein and other beneficial components (such as polyphenols and lutein). The composition, and especially the protein, is preferably in powder form, and has a high protein content and high purity, as well as other unique advantages described below. Because of its advantages, the protein is particularly useful in food products. The invention also entails methods for obtaining the protein concentrations from sweet potato plant leaves.

BACKGROUND OF THE INVENTION

There is presently tremendous demand for food products with higher protein delivery (Technavio 2017) from alternatives to traditional meat and fish sources. And while dairy whey (whey protein concentrates, isolate) and egg-based proteins are common alternatives, both have human intolerances and many people wish to lower their intake of animal-sourced ingredients. The latter is due to broader issues concerning sustainability and the ethical treatment of animals (Wiley 2015). The result is a growing need for suitable plant protein for consumption by humans and other mammals or even non-mammals (e.g., birds and fish). Currently, this demand is met primarily by fortification from two main sources, soybeans (including soy protein concentrates, isolates) and wheat based protein.

Though soy proteins are a market dominator, soy contains high levels of phytoestrogens, which are of concern to many consumers. Specifically, animal studies suggest a disruption of brain sexual differentiation and abnormal development of reproductive tract, along with co-diseases which result from phytoestrogen consumption (Patisaul 2010). There is a need for plant-based protein sources that can perform well in foods by not only providing this desired boost in nutritious protein, but also which function properly in terms of texturization, flavor, appearance, and stability of foods.

While leaf protein is composed of hundreds of enzymes, its protein content is dominated by the single polypeptide complex of rubisco. Rubisco (ribulose-1,5-bisphosphate carboxylase/oxygenase), the main carbon fixing enzyme found in nearly all plants, is the most abundant protein on earth, comprising nearly half on average of the total protein content of most leaf sources (Kawashima and Wildman, 1970). Many chloroplast proteins, including rubisco, are highly conserved at the gene and protein levels (Sane and Amla, 1991). Thus, rubisco is much the same protein in all green leafy plants, with only slight amino acids changes from species to species.

The general difference in nutritional value of protein derived from grains, legumes, and leafy vegetables can readily be understood by comparing their methionine and lysine contents (Edelman and Colt 2016). Grains and most other monocot food plants (ex: wheat, corn, and rice) are generally poor in lysine while the dicot legume pulses (ex: soy, chickpea, and lentil) are often lacking in methionine. Leaf sources on the other hand align into the FAO standard quadrant with the animal foods (meats, milk, eggs) in protein nutrient quality. The amino acid profile of rubisco for nutritional application is such that leaf protein from any edible source is nutritionally on par with egg white for human food value.

Leaf proteins and rubisco as a food ingredient source have been suggested. (Barbeau and Kinsella 1988) But very little work has been conducted to isolate food-quality, high functionality and good tasting/appearing proteins from leaf sources. Leaf proteins have potential for several key functionalities in food applications, including gelation, emulsification, foaming, and solubility (Fantozzi and Sensidoni, 1983; Sheen 1989, 1991a,b; Sheen and Sheen 1985; Kung et al. 1980; Fu et al. 2010). One report noted that strong textured meringues could be made from rubisco. This particular gelling/foaming application has only ever been associated with high quality egg white, a quite valuable food protein commodity; even dairy whey proteins which gel almost as well as egg white have never exhibited this unique functionality.

One approach to leaf protein fractionation was based entirely upon crystallization of rubisco from green tobacco leaf extracts, a process that is both time- and space-consuming and which places rigorous limits on the freshness of the leaf. (Wildman 1983) In the ensuing decades, ultrafiltration as a commercial process for protein fractionation has advanced dramatically, both in terms of efficiency (lowered cost) and control, mainly as a result of the commercial emergence of the dairy whey processing industry (Baldasso 2011). More recently published attempts to isolate protein from tobacco leaves, as well as from many other plant leaf sources, almost exclusively have depended upon this important refining step, thus eliminating the need to crystallize out the protein(s) of choice (Bals 2011).

Still, there remains a lack of non-manipulated whole-leaf protein that is high in pure protein content, that has an origin and non-manipulated taste that is desirable to consumers, and that is in a powder form easily dispersible and/or soluble in aqueous media. There is similarly a need for a cost-effective, efficient, method to make such a leaf protein powder, which process uses a minimum of steps and does not require toxic or non-desirable chemicals. Additionally, there is a need for compositions containing both good protein content and other beneficial components such as polyphenols, luteins, and the like, in powder form.

Sweet potatoes are a green leafy plant that can produce more protein per acre via their leaves than can be produced from grain crops, such as soy (Smit 2013). Leaves from sweet potato crops are generally wasted upon harvest of the tuber. Advantageously, sweet potatoes leaves can be harvested at the time of tuber harvest resulting in no adverse effect on tuber production. The protein content of sweet potato leaves ranges from 17-30% of dry weight. (Sun, 2014)

Due to past difficulties in the ability to fully extract and purify protein from green leafy plants, to date leaf proteins have been considered fit only for marketing into animal feed. A case in point is alfalfa leaf (Bals 2011). Yet the net financial return for this latter application is relatively low, even given the potentially large tonnage that might be marketable from such a source. Likewise, conversion to human food via feeding animals is recognized to be both economically and environmentally wasteful, as well as energy intensive (Pimentel 1997).

Sweet potato leaves in particular have presented unique problems for extraction and purification of proteins or other leaf components. Past researchers have reported that protein extraction and purification from these leaves are almost completely hampered because beginning early in the extraction process (e.g., beginning with disruption of the leaves) there is invariably encountered a thick, sticky—even slimy—extraction phase and product, which makes further extraction and purification difficult. (See Walters, 1978) Because of the thick gooey state of the sweet potato leaves juice and particulates, standard methodology such as separations by filtration or centrifugation are greatly impeded. The high viscosity of the juice and particulates entirely clogged centrifuges, and at best, caused such poor flow rates as to prevent proper spinning down of the of the liquid. Even if such a product could be dried down, spray drying would be nearly impossible. The yield and purity of the resultant leaf protein was significantly lower than desired. The inventors believe the cause of this phenomenon to be high molecular weight polysaccharides that form a viscous mucilage upon release from the leaf cell walls. This high molecular weight polysaccharide mucilage in sweet potato leaves poses a significant problem for extraction and purification of the leaf proteins. So, although sweet potato leaves are available in abundance and appear to be a source of leaf protein, obtaining the protein in reasonable purity and yield has heretofore been too difficult.

SUMMARY OF THE INVENTION

This invention addresses these needs, and provides a leaf protein in dried form that has properties and a structure that is advantageous in additional and unforeseen ways. Specifically, we have developed a composition containing a high concentration of sweet potato leaf protein. The inventors have unexpectedly been able to obtain a concentration of sweet potato leaf protein in powder form, which includes non-manipulated whole leaf protein of high content and purity. The composition is unlike other known purified plant proteins or anything found in nature. The dried composition is functional in food systems, acceptable in taste and appearance, is easily and fully dispersible in water or other aqueous media, and has other unexpected advantages described below. Unique methods by which to produce the protein concentrate are also described.

Unlike any other leaf protein compositions, our novel protein composition is derived solely from sweet potato leaves. This alone is novel, since prior to this discovery, sweet potato leaf proteins have not been able to easily be extracted and purified—especially not by non-manipulated methods, and having good purity, and with good yield. This addresses the need to utilize only leaf sources which are acceptable to consumers, and achieve a protein source that is free of traces of toxic chemicals (having avoided the use of any toxic chemicals in the process). Sweet potato leaves are cost efficient and quite readily available since they are plentiful during several seasons, and at present are wasted at time of harvest of the tubers.

The inventors were able to overcome the obstacles unique to extraction and purification of sweet potato leaf protein, to achieve a derivative product that (1) is high in protein content or protein purity (e.g., between 21-32% by weight, or at least 26% by weight), and (2) is in dried form, preferably a powder, which is easily dispersible and soluble in aqueous media. In preferred embodiments, the dried down product is characterized in that the high molecular weight viscous mucilage-forming polysaccharides that form a viscous mucilage upon release from the leaf cell walls are almost completely degraded enzymatically, and thus the product has a low viscosity when mixed in aqueous media.

It is preferred that the protein concentrate composition is at least substantially free, and preferably at least completely free (or having only trace amounts) of the high molecular weight polysaccharides that form a viscous mucilage upon release from the leaf cell walls. As described above, these high molecular weight mucilage-forming polysaccharides are distinctive to sweet potato leaves, and are a hindrance to the extraction and purification of protein. As described in detail below, the reduction or absence of these particular polysaccharides is helpful to facilitate extraction, recovery, purification and good yield of the soluble leaf proteins. It is also helpful to facilitate the low viscosity of the protein concentrate when it is mixed in aqueous media.

This combination of features results in a sweet potato leaf derivative protein composition in powder form, that has a low and useful viscosity when mixed in liquid.

In one main embodiment, this invention entails a sweet potato leaf protein concentrate dried-down product (e.g., powder) which is dispersible and/or soluble in aqueous media. By "concentrated" protein or "protein concentrate" in the context of this invention, it is meant that there is a higher concentration of sweet potato leaf protein compared to the concentration of protein in the leaf in its natural state. For instance, a high concentration may be between about 21% to about 32% protein of the weight of the total dried down composition. The protein concentrate is unnatural in that it could not be found in nature in such a concentration and purity. This is especially the case with protein obtained from sweet potato leaves, which presents unique challenges to extraction and purification to take the form of an isolated, concentrated protein or protein concentrate, alone or in combination with other desired components (e.g., polyphenols). In order to obtain the level of protein content, a derivative composition of sweet potato leaves was created. The sweet potato leaf protein may be obtained from any plant classified as *Ipomoea batatas*. The sweet potato leaf protein may be obtained from any known cultivar or variety (e.g., Covington and Beauregard varieties).

The sweet potato leaf protein concentrate powder (hereafter referred to as "protein concentrate") preferably has a protein content (or purity) of over about 21%, or preferably over about 24%, preferably over about 26%, preferably over about 30%, preferably between about 26% to about 30%, or preferably between about 26 and about 32% by wt. Preferably, the protein concentrate has qualities of low viscosity, such that when the powder is added to aqueous media to form a mixture of 10% solids, the viscosity of the mixture is about 300-350 centipoise (cP). By "mixture" is intended solution, dispersion or any form by which the protein concentrate is combined with an aqueous-based media. The protein concentrate powder is preferably at least 90% dispersible in aqueous media, and/or at least 85% soluble in aqueous media.

Preferably, the protein concentrate has a rubisco content (or purity) between at least 21% to about 32% by wt of the total composition.

Preferably, most or even substantially all of the protein concentrate is not denatured or degraded (e.g, intact in proper native conformation). This is especially true of the product produced by the methods described herein, because in most cases the product is not sufficiently exposed to heat, so that the protein would not be denatured. Although the pH shifts that occur in the process can affect denaturation, this is largely reversible when carried out cold as in our process (to prevent aggregation). Preferably, most or even substantially all of the rubisco present in the protein concentrate is not denatured. Preferably, at least 80%, at least 90%, at least 95%, or at least 97%, or at least 99% of the protein is not denatured. Conversely, no more than about 1%, or 3%, or 5%, or 10%, or 20% of the protein is denatured. Preferably, at least 80%, at least 90%, at least 95%, at least 97%, or at least 99% of the rubisco present in the protein is not denatured. Conversely, no more than about 1%, or 3%, or 5%, or 10%, or 20% of the rubisco present in the protein is denatured.

The quality of the protein (and rubisco especially) can be measured by differential scanning calorimetry DSC. Because of the high quality/low denaturation of the protein, the desired properties of foaming, gelling, and dispersability are increased. Foaming can be measured using standard techniques, for instance, by percentage overrun (increase in volume; up to 100% or more) when whipped under typical shear conditions (e.g, by mixer). Our protein concentrates have high foaming volume, and good foam stability (e.g., overrun stable within 10% for an hour or more at room temperature). Our protein concentrates have excellent gelling properties, and can hold a shape indefinitely. Gelling can be measured using standard techniques, such as by conversion of a dispersion of 8% protein or more to a gel after cooking to 90 C and cooling. Dispersability is also excellent, with at least 75% of the protein concentrates maintained in aqueous phase after vigorous blending and holding for 15 minutes.

The sweet potato leaf protein composition is a unique combination of properties, that gives it advantages over other leaf protein extractions—it has good protein content, good protein purity, but yet is palatable, bland-tasking, and light-colored (i.e., appealing in color). Preferably, the protein concentrate requires no de-odoring, de-coloring or de-flavoring, and/or requires no reduction of organoleptic properties, and/or requires no reduction of astringency in the production thereof.

The color and smell of the non-manipulated end product is advantageous because it will appeal to consumers. It is a non-manipulated composition, meaning that no chemical or mechanical manipulation (e.g., extraction, precipitation, extra purification, etc.) is needed in order for the dried protein concentrate to have the properties of bland and pleasant taste, light color, high purity, and dispersibility and/or solubility.

Preferably, the color is light in value and of a hue and chroma associated with healthy vegetables, such as orange (associated with beta carotene) or red-purple-blue (associated with anthocyanins), or else sufficiently light and low in hue to be blended with other food constituents and not impart off color or undesired darkening. Preferably, the color has a lightness range between 58.5-78.5, as measured by a standard colorimeter. See FIGS. 2 and 3.

Preferably, the taste of the protein concentrate is pleasant to a majority of consumers (especially when identified as being of sweet potato origin), using a standard taste panel.

Preferably, no unpleasant odor is noticeable, as determined by a standard organoleptic panel.

In one variation, the protein concentrate has less than 10% fat, 10% carbohydrates, and 10% ash. In this variation, preferably, the protein concentrate is isolated in the absence of all but trace amounts leaf components of fat, carbohydrates, and ash.

The protein concentrate is in a dry form, preferably in a particulate, preferably in powder form. Preferably, the protein concentrate has less than 10% moisture, or between 5-8% water residual moisture.

Preferably, the protein concentrate is heat stable in aqueous media.

Preferably, the protein concentrate is shelf-stable at room temperature for at least 3 months and preferably at least 6 months in the absence of stabilizers or additives for maintaining the product in solution or dispersion. Preferably, the product is stored at room temperature in filled sealed gas impermeable containers at room temperature (25 C). The protein concentrates are advantageous because, after 3 months or even 6 months, they will have little (less than 10%) change in any functional properties described herein, no noticeable (by organoleptic panel) change in flavor or color, no greater than 10% change in any nutritional content of interest (polyphenols, anthocyanins, carotenoids or other bionutritional components) or other change in measurable oxidative rancidity.

Preferably, the protein concentrate has a taste profile that is acceptable or preferably desirable or pleasant, as measured using standard methods such as those described below. Preferably, the protein concentrate has an odor profile that is acceptable or preferably desirable or pleasant, as measured using standard methods such as those described below.

Preferably, the protein concentrate powder has additional components that are naturally present in sweet potato leaves but would normally be filtered out in the process of obtaining the proteins in a concentrated form. In particular, it is often desired for the powder composition to include at least one polyphenol. Polyphenols are micronutrients that contain antioxidants and offer potential health benefits, such as improving or helping treat digestion issues, weight management difficulties, diabetes, neurodegenerative disease, and cardiovascular diseases, to name a few. Sweet potato leaves are known to include a number of dietary polyphenols such as anthocyanins and phenolic acids. (See Fu et al., 2016). Preferably, the sweet potato leaf protein concentrate powder contains one or more polyphenols such as hydrobenzoic acids, hydroxycinnamic acids, flavonoids, stilbenes, and lignans. In particular, the polyphenols could include one or more of hydroxycinnamic acids such as di-caffeoylquinic acids, caffeoylquinic acids, quercetin-3-glucoside, p coumaric acid and mixtures thereof.

Other examples of phenolic acids are caffeic acid (CA) and 5 kinds of caffeoylquinic acid derivatives: 3-mono-O-caffeoylquinic acid (chlorogenic acid, ChA), 3,4-di-O-caffeoylquinic acid (3,4-diCQA), 3,5-di-Ocaffeoylquinic acid (3,5-diCQA), 4,5-di-O-caffeoylquinic acid (4,5-diCQA), and 3,4,5-tri-O-caffeoylquinic acid (3,4,5-triCQA) which are known to have various kinds of beneficial physiological functions.

Other polyphenols might include protocatechuic acid, gallic acid, coumaric acid, caffeic acid, ferulic acid, curcumin, secoisolariciresinol, kaempferol, quercitin, myricetin, apigenin, luteolin, daidzein, genistein, naringenin, eriodictyoo, hesperetin, pelargonidin, cyanidin, delphinidin, petunidin, malvidin, catechins, and gallocetechin.

Preferably, the polyphenol content is between about 3-5 mg/g (dry weight) in the protein concentrate powder.

In addition, the protein concentrate can contain biologically active anthocyanins known to be beneficial to human health raw derived from the raw leaf (Islam 2006). These anthocyanins may be of the acylated cyanidin and peonidin types.

In the alternative, or in addition, the protein concentrate can contain radical scavenging activity, antimutagenic activity, anticancer, antidiabetes, and antibacterial activity which may be beneficial for human health.

The protein concentrate are nutritionally advantageous. Preferably, the protein concentrate has significant amounts of beta-carotene, a vitamin necessary to good human health.

Depending on the desired use of the protein concentrate powder, polyphenols may be deemed as undesirable contaminants—if so, as described below, it is possible to remove them. Our invention contemplates protein concentrate powders with and without polyphenols present. To that end, in one alternative embodiment, however, the protein concentrate does not bind at all, or does not substantially bind, with polyphenols.

Other components that the sweet potato leaf protein concentrate powder may contain include one or more of lutein, beta-carotene, biologically active anthocyanins (such as the acylated cyanidin and peonidin types), and compounds having radical scavenging activity, antimutagenic activity, anticancer, antidiabetes, and/or antibacterial activity.

In another embodiment, the invention entails a composition comprising the protein concentrate in any of its forms or preferred embodiments described herein. Preferably, the composition also contains an aqueous solution. The aqueous solution can preferably include, besides water, a food product, a food supplement, and the like.

The protein concentrate powder, in any of the variations described herein, is very compatible for use as protein supplement for a food or beverage. Its high protein content, good dispersibility, good solubility, low viscosity in aqueous media, and pleasant flavor and color make it ideal for these purposes. Polyphenols are also a particularly desirable components for their beneficial antioxidant and other health benefits. The protein powder offers a more healthy alternative protein to humans and animals alike, and can be used in products which clearly have health advantages for childhood development (Patisaul 2010).

To that end, in another embodiment, the invention entails food products or supplements that contain the protein concentrate. In particular, one embodiment entails a protein beverage, or a protein supplement for a food or beverage, comprising the protein concentrate described herein.

In another embodiment, in the food product or supplement, the protein concentrate, especially rubisco present, is capable of forming a gel, or forming a whip, or forming a foam in a food material.

One embodiment entails a gelling agent suitable as a food supplement, comprising the protein concentrate described herein.

Another embodiment entails a whipping agent or a foaming agent suitable as a food supplement, comprising the protein concentrate described herein.

Additional unique properties and characteristics of this sweet potato leaf protein concentrate are described in some detail below. For several reasons, our leaf protein concentrate is a superior and less expensive alternative to current known protein powders.

Similarly, the processes for obtaining the dried sweet potato leaf protein concentrate are themselves unique. Several processes are described below. Just one advantage of the processes is that they can use bio waste from large scale farmed sweet potatoes to produce a novel protein powder having significant competitive advantage. Additionally, it may be plausible to harvest the leaves multiple times per year with minimal effect on the yield of tubers (Van An 2003). This is not only convenient but in fact important for processing as currently the best method for optimizing protein extraction depends on the leaves being as fresh as possible.

The majority of research published on leaf protein extraction to make protein concentrates is focused on use of either tobacco or alfalfa. A few other novel leaf sources have been tested in passing with little data reported. Tobacco presents difficult acceptance issues from both consumers and regulatory agencies as it is not regarded as a suitable food source. Alfalfa would not face this hurdle, but published attempts at alfalfa protein extraction show the difficulty of obtaining a protein product that is not contaminated with high levels of chlorophylls and polyphenols, resulting in an unpleasant grassy flavor. Alfalfa also has some significant value as an animal feed source, but not much value as a protein source for humans.

Unlike soy leaves, which also might be considered consumer-friendly, sweet potato leaves can be harvested without damage to the intended food crop (soybeans or sweet potato tubers). In the normal course of sweet potato harvesting, it is common practice to mow the leaves 2-3 days before harvest to allow the tubers to begin curing, thus minimizing tuber damage during harvest. Therefore it would be relatively simple to harvest the leaves during mowing and process them for protein as a value added product rather than treating them as a low value waste stream. This would offer an economic boost that many agricultural producers desperately need in the current climate of falling commodity prices (Schnepf 2017).

However, as noted above, extraction and purification of proteins from sweet potato leaves has proven difficult. Upon initial disruption of the leaf cell walls and release of the leaf components, even if in aqueous solution or a buffer solution (either acidic or alkaline), high molecular weight mucilage-forming polysaccharides present in the leaves almost immediately form a highly viscous mucilage. This mucilage impedes standard extraction methods—in fact brings the extraction to nearly a halt, and the yield to almost nothing.

The inventors attempted various ways to obtain a sweet potato leaf protein concentrate of good purity and yield. Two methods, each unique in its own right, brought good success in different aspects of protein content and yield. All other methods tried failed to yield a protein concentrate of reasonable purity.

In a first method embodiment, the invention entails a method or process for producing the sweet potato leaf protein concentrate in a dried form (e.g., powder), having the qualities described in this paper. The main steps of the process comprise the following:

a) simultaneously disrupting the cell walls of plant leaves and contacting sweet potato leaf proteins (both rubisco and non-rubisco proteins, preferably soluble) released from the disrupted plant leaves with a buffer solution;

b) removing from the buffer solution produced in step (a) substantially all cellulosic material to produce a buffer solution containing plant chloroplast material and the soluble leaf proteins, (preferably under conditions so as to minimize non-protein components present in the buffer solution and minimize breakdown of non-protein material into the buffer solution) and wherein the soluble leaf proteins remain solubilized in the buffer solution;

c) removing from the buffer solution produced in step (b) at least 60%, or at least 70%, or at least 80%, or at least 90% or at least 95%, or at last 99%, or substantially all of the plant chloroplast material to produce a buffer solution containing the soluble leaf proteins, which proteins remain solubilized therein; and d) drying down the solubilized soluble leaf proteins from the buffer solution, to produce a protein concentrate in dried form (e.g., powder).

Preferably, in step a) the disrupted leaf materials and the leaf proteins are exposed to the buffer solution, and the leaf proteins solubilize and are kept in the buffer solution.

Preferably, the buffer solution has a solute concentration between 0.025M and 0.3M. Preferably, the buffer solution is present in a buffer-to-leaf ratio of greater than approximately 1:2 but not more than approximately 8:1. Preferably, the buffer solution has a pH between 6.5 and 9.0. Preferably, the buffer solution has a buffering region that is effective within a pH between 6.5 and 9.0.

Preferably, the buffer solution is phosphate buffer. Preferably, the buffer solution comprises a chelating agent and/or a reducing agent.

Preferably, the process is conducted throughout at a temperature between about 0°-about 25° Celsius.

Preferably, step b), or step c), or both occurs without adsorption on a solid support or removal by filtration of the soluble leaf proteins.

Preferably, throughout steps (a), (b) and (c) the leaf proteins remain solubilized and kept in the buffer solution while cellulosic material and plant chloroplast material are sequentially removed therefrom.

Preferably, in step (a) the cell walls of the leaves are disrupted by chopping, milling, grinding or crushing the leaves, pulping, maceration procedures, mechanical pressure, rollers or homogenizing.

Optionally, after step (a) the leaf proteins are maintained in the buffer solution for up to twenty-four hours. Optionally, the leaf proteins are maintained in the buffer solution at ambient temperature or lower.

The buffer solution should be suitable for protein extraction. Examples of a buffer solution, or components for a buffer solution, are any of these alone or in combination: sodium phosphate dibasic and potassium phosphate monobasic ($Na_2HPO_4$—$KH_2PO_4$), potassium phosphate monobasic/sodium hydroxide, sodium hydroxide/citric acid, acetic acid/ammonium acetate, potassium hydroxide/potassium phosphate monobasic, citric acid/disodium phosphate, potassium phosphate monobasic/potassium phosphate, dibasic, potassium acid phthalate/sodium hydroxide, potassium carbonate/potassium tetraborate/potassium hydroxide/disodium EDTA dihydrate, giordano's buffer, sodium acetate trihydrate/sodium chloride, tris(hydroxymethyl)aminomethane (Tris), EDTA/Tris/HCl, 2-amino-2-(hydroxymethyl)-1, 3-propanediol/Tris, Tris/EDTA, ammonium chloride/ammonium hydroxide, HEPES/NaCl, imidazole, phosphate, N-morpholinopropane sulfonic acid (MOPS), N-tris(hydroxymethyl)methyl-2-aminoethane sulfonic acid ("TES"), triethanolamine, and N-tris(hydroxymethyl)-methyl-glycine ("Tricine").

Preferably, the buffer contains a chelating agent. Examples of chelating agents include EDTA, EGTA, HEDTA, DTPA, NTA, calcium citrate, calcium diacetate, calcium hexametaphosphate, citric acid, gluconic acid, dipotassium phosphate, disodium phosphate, isopropyl citrate, monobasic calcium phosphate, monoisopropyl citrate, potassium citrate, sodium acid phosphate, sodium citrate, sodium gluconate, sodium hexametaphosphate, sodium metaphosphate, sodium phosphate, sodium pyrophosphate, sodium tripolyphosphate, stearyl citrate, tetra sodium pyrophosphate, calcium disodium ethylene diamine tetra-acetate, glucono delta-lactone, potassium gluconate and the like, and their analogs, homologs and derivatives.

Preferably, the buffer contains a reducing agent. Examples of reducing agents include 2-mercaptoethanol, 2-mercaptoethylamine-HCL, cysteine-HCL, Ellman's reagent, BME, DTT, glutathione, cystein, Tris (2-carboxyethyl) phosphine hydrochloride, TCEP disulfide, n-ethylmaleimide, TCEP-HCL, ferrous ion, lithium aluminum hydride ($LiAlH_4$), nascent hydrogen, sodium amalgam, sodium borohydride ($NaBH_4$), stannous ion, sulfite compounds, hydrazine, zinc-mercury amalgam (Zn(Hg)), diisobutylaluminum hydride, lindlar catalyst, oxalic acid ($C_2H_2O_4$), dithioerythritol, thioglycolate, glutathione, cysteinem ascorbate, and their analogs, homologs and derivatives.

Preferably, in step (b) the cellulosic material is removed using a screw press, fiber filter, fly presser, blender, mechanical presser, mechanical dewatering device, or crusher.

Preferably, step b) is carried out under conditions that the buffer solution produced by step b) does not contain non-protein plant material in sufficient amount to substantially hinder removal of plant chloroplast material in step c).

Optionally, and preferably, as described herein, optimum protein extraction is obtained by adjusting buffer type, pH (or combination of pH), extraction time and cell disruption technique. Preferably, as described herein, purity and yield are optimized by inclusion of one or more of the further steps:

i) Before (or during) step a) or step b), reducing pH in buffer solution to reach acidic or slightly acidic conditions, so that proteolysis is reduced, and then prior to step b) setting pH of buffer solution to a neutral or generally neutral condition;

ii) Before step a), carrying out any other pretreatment step, that is suitable for use with sweet potato leaf proteins;

Briefly heating the buffer solution to precipitate and facilitate removal of non-protein leaf components, which brief heating takes place before or after step c, or both. (Heating should be brief enough that no significantly denaturation of the protein takes place.)

iii) After step c), filtering the buffer solution of step c) via in depth filtration; and/or iv) After step c), filtering the buffer solution of step c) via ultrafiltration.

Preferably, in iv) the depth filtration conditions are suitable to increase purification of the product, and are suitable for sweet potato leaf protein.

Preferably, in step (c) the chloroplast material is removed using a centrifuge or vacuum filtration.

Preferably, the end product includes significant amounts of beta-carotene. However, under some circumstances, the removal of beta-carotene is desirable. If that is the case, the process includes the further step after step b) or c) of substantially removing all beta-carotene.

Preferably, the end product protein concentrate is substantially free of chlorophyll.

In one variation, the process includes the further step of minimizing interaction between polyphenols and the leaf proteins. Preferably, minimizing interaction between polyphenols and the leaf proteins is achieved by using a buffer of 0.025 molar potassium metabisulfite in step a). Alternatively, minimizing interaction between polyphenols and the leaf proteins is achieved by the further step prior to or after step b) of selectively removing polyphenols from the buffer solution via an ethanol extraction.

Preferably, the process includes the further step after step b) of an alkaline extraction of the buffer solution to precipitate non-water soluble protein.

Preferably, the process includes the further step after step c) of purification of the buffer solution to precipitate rubisco.

Preferably, in step (d) the drying down is done by spray drying, vacuum drying, or freeze drying.

Preferably, the process comprises the further steps between step (c) and step (d):

precipitating without denaturing soluble leaf proteins by conducting an isoelectric point precipitation on the buffer solution containing the solubilized leaf proteins, for up to 40 minutes at a pH suitable for sweet potato leaf proteins or within 0.5 pH units;

removing any supernatant; and resuspending the precipitated soluble leaf proteins in the buffer solution.

The process produced a powder having a protein content of between 26-28% by weight, and a total yield of protein of just over 1% (based on weight of dry leaf extracted).

Preferably, the process produces a dried-down protein product that is at least 90% dispersible and/or at least 85% soluble in aqueous media.

Preferably, the process produces a dried-down protein product which has less than 10% fat, 10% carbohydrates, and 10% ash. Preferably, the process produces a dried-down protein product which is concentrated in the absence of all but trace amounts leaf components of fat, carbohydrates, and ash.

Notably, by this first method polyphenols are removed from the final protein product. The protein concentrate did not contain polyphenols (or only trace amounts), since these were extracted by the buffer.

Preferably, the process produces a dried-down protein product which has a water content of less than 10%, and more preferably between 5-8% residual moisture.

Preferably, the process produces a dried-down protein product wherein substantially all of the protein concentrate is not denatured (e.g., no more than about 10% wt or preferably no more than 7% or no more than 5% or no more than 3% or no more than 1% of the protein concentrate is not denatured). Preferably, the process produces a dried-down protein product wherein substantially all of the rubisco is not denatured (e.g., no more than about 10% wt or preferably no more than 7% or no more than 5% or no more than 3% or no more than 1% wt of the rubisco is not denatured).

As is well known, the isoelectric point is the pH at which a molecule or surface carries no net electrical charge and is its point of minimum solubility. Isoelectric point determination is a well-known procedure which can be performed by any of several recognized methods (Yang and Lange, 1987).

This method did produce some useful product, but there were major problems during trials and with the end-product. First, the overall yield was low, only about 1% of dry leaf weight, even though the protein content of recovered powder was between 26-28% by wt. of the total powder weight. Second, there was significant protein loss during the depth filtration step. Finally, there were problems in getting the sweet potato leaf juice through the centrifuge, because the thick, viscous consistency of the juice and particulates resulted in poor flow rates through the centrifuge.

It is believed that the problems during the centrifugation process are due to the high molecular weight mucilage-forming polysaccharides which, when released during leaf disruption, is causing the centrifuge to be unable to spin down the liquid properly. (Also see Walters 1978). Hence, the yield was surprisingly low.

This first method embodiment was successful to produce the unique sweet potato leaf protein concentrate. Although the yield was low, the protein that did get recovered had the above-described characteristics of (1) a high protein content or protein purity (e.g., over 21% by weight), and (2) is in dried form, preferably a powder, which is easily dispersible and soluble in aqueous media.

In a second method embodiment, the inventors were able to solve many of the problems and disadvantages of the first method embodiment. In this second method, the invention entails a method or process for producing one or more of the sweet potato leaf protein concentrates in a dried form (e.g., powder), as described herein. The main steps of the process comprise the following:

1) disrupting the cell walls of plant leaves and contacting soluble sweet potato leaf proteins released from the disrupted plant leaves with an aqueous solution having an acid pH (that is, less than pH of 7, and preferably having a pH between 4 and 6), so that soluble leaf proteins are solubilized in the aqueous solution;

2) adding to the aqueous solution at least one enzyme that catalyzes the breakdown and/or hydrolysis of carbohydrates, and adjusting the pH if needed to be acidic or remain acidic (preferably between 4 and 6), 3) extracting the aqueous solution at a basic (or alkaline) pH (that is, greater than a pH of 7, and preferably between 10 and 13, or the pH which optimizes protein extraction);

4) removing from the aqueous solution produced in step (3) substantially all cellulosic and starch material to produce an aqueous solution containing plant chloroplast material and the soluble leaf proteins, 5) adding to the aqueous solution of step (4) at least one enzyme that catalyzes the breakdown and/or hydrolysis of carbohydrates, and adjusting the pH to an acidic pH (preferably between 4 and 6), 6) filtering (e.g., by ultrafiltration and/or diafiltration) the aqueous solution of step (5), wherein throughout steps (1)-(6) the soluble leaf protein remains solubilized in the aqueous solution, and 7) drying down the soluble leaf proteins from the aqueous solution of step (6), to produce a sweet potato leaf protein concentrate in dried form.

Steps 1) and 2) can be combined into a single step. Or Step 2) can be carried out simultaneously to step 1), or immediately thereafter, or within 5 minutes or within 30 minutes. For instance, Step 1) could immediately precede adding the aqueous solution of Step 2), or the leaf disruption could be done simultaneous with addition of the aqueous solution (combined Steps 1 and 2). The enzyme could already be in the aqueous solution as it is added to the crushed leaf matter, or the enzyme could be added immediately after the aqueous solution is added. It is preferred that the time between Steps 1) and 2) be as short as possible to minimize degradation of protein. Both mechanical and enzymatic action are being used to disrupt the tissue before adjusting to a higher pH (Step 3) for a maximized protein extraction. But of course protein begins to extract (move from cells into free liquid) as soon as any free liquid exists.

Optionally, and preferably, the enzymatic steps will be followed by appropriate incubation times and temperatures, as would be known by someone skilled in this art.

Preferably, in Step 2 the at least one enzyme can be any enzyme that facilitates the hydrolysis of polysaccharides into monosaccharides (e.g., such as a carbohydrase or enzyme that functions in a similar way to a carbohydrase). Preferably, the enzyme is selected from the group consisting of arabanase, cellulase, beta-glucanase, hemicellulose, xylanase, and pectinase, as well as amylase. For example, the cellulosic mixture Novozyme Viscozyme L has shown good results, and includes a wide range of carbohydrases including arabanase, cellulase, beta-glucanase, hemicellulase and xylanase. Pectinases can be added to break down branched pectin-like substances found in plant cell walls. This step is done at an acidic pH range, preferably between 4 and 6, and preferably near 6.

Preferably, Step 4 is carried out by centrifuge.

Preferably, in Step 5 the enzymes can be any enzyme that facilitates the hydrolysis of polysaccharides into small (<10 Kda) monosaccharides (e.g., such as a carbohydrase or any enzyme that functions in a similar was to a carbohydrase). The enzymes are preferably selected from the group consisting of beta-glucanase and amylase (e.g., alpha amylase), as well as arabanase, cellulase, hemicellulose, xylanase, and pectinase pectinase. Especially preferred is alpha amylase. Other enzymes can also be useful in this step. For example, the enzymes in Step 2 may still be (and preferably are) active in Step 5. This step is done at an acidic pH range, preferably between 4 and 6, and preferably near 6.

In Step 6, the filtering should be effective to filter at least some soluble leaf protein from non-protein components. Standard techniques can be useful for this. For instance, preferably in Step 6 the filtration is conducted by ultrafiltration (UF) and diafiltration (DF). By "ultrafiltration" it will be understood to mean filtration by a membrane filtration in which forces like pressure or concentration gradients lead to a separation through a semipermeable membrane. Suspended solids and solutes of high molecular weight are retained in the retentate, while water and low molecular weight solutes pass through the membrane in the permeate (filtrate). Standard ultrafiltration techniques can be used. The membranes contemplated for this process must be suitable to remove all material smaller in size than the soluble leaf proteins targeted. In general, the ultrafiltration membranes will have a pore size one tenth that of the particle size to be separated. In general, the membranes will have a molecular weight cut-off (MWCO) of no greater than 5-10 kDa.

Another preferred filtration technique is diafiltration. When used, for efficiency, the diafiltration is preferably carried out immediately after an ultrafiltration using the same equipment and membranes as the ultrafiltration. By "diafiltration" it will be understood to mean a dilution dilution followed by reconcentration by UF process that involves removal or separation of components (e.g., permeable molecules like salts, small proteins, solvents etc., of a solution based on their molecular size by using micromolecule permeable filters in order to obtain pure solution. Standard diafiltration techniques can be used. Someone skilled in the art would be able to determine how many dilution stages/injections of dilution are necessary to follow the ultrafiltration, so as to remove the undesired components from the protein target (and other target components).

For the filtering in Step 6, parameters such as flux, pressure, pore size, time, temperature, etc. are adjusted so as to have a flux that effects throughput that is adequate relative to membrane area being used (main cost), with little or no fouling for extended run periods, and minimal loss of the proteins of interest.

In all the steps, and throughout the process until drying down, it is important to keep the leaf proteins solubilized in solution.

Preferably, the product of the process is a dried-down protein product having a protein content of between about 21% to about 32% by weight. Preferably, the product is an concentrated protein powder which is dispersible and/or soluble in aqueous media. For example, dispersibility is at least 90%, and solubility is at least 85%.

The yield of this process was at least about 7%, 8%, or about 10%, or up to about 12% of protein concentrate powder, where over 21% (up to about 32%) of protein content was recovered, based on weight of the dry leaf extracted. This represents a good protein content recovery and a significantly higher yield compared to the first method embodiment.

In this process, there is no buffer solution such as is required in the first method embodiment. Instead, an aqueous solution is used, which affords several benefits. Besides the advantage of cost savings (buffer solutions can be costly, especially for large batch productions), the aqueous solution does not remove polyphenols, such as the buffer solution does in the first method embodiment. The polyphenols remain and can bind freely to soluble leaf proteins within the solution. Whereas the first method embodiment is advantageous when it is desirable to remove polyphenols, this second method embodiment is advantageous when it is desirable to have polyphenols in the end product (e.g., for health benefits, as described above). The polyphenols may be any of those found naturally in sweet potato leaves, such as those described herein—and in particular, hydrobenzoic acids, hydroxycinnamic acids, flavonoids, stilbenes, and lignans. In particular, the hydroxycinnamic acids can be di-caffeoylquinic acids, caffeoylquinic acids, quercetin-3-glucoside, p coumaric acid and mixtures thereof.

In addition, in this second method embodiment, a critical step is the use of at least one enzyme in Steps (2) and (5). The enzymes are effective to enhance soluble protein release from plant organelles, reduce viscosity by facilitating hydrolysis of the high molecular weight mucilage-forming polysaccharides into monosaccharides (responsible for the slimy high viscosity), and ultimately help recovery and yield of the leaf proteins by reducing molecular weight of the polysaccharides (and any other large carbohydrates) such that they are removed during the last filtration.

In both Steps (2) and (5), the addition of the enzyme causes breakdown and/or hydrolysis of the high molecular weight mucilage-forming polysaccharides into monosaccharides—which results in a significant reduction in and preferably a complete lack of retention of the mucilage. Without the formation of the mucilage, the flow rate of the leaf juice has a low viscosity and can flow easily through the rest of the process including all filtration equipment. In addition, in Step (2) the addition of the at least one enzyme releases more soluble proteins prior to the extraction/filtration Steps (3) and (4). The enzymes break down many different cellular structures to enhance protein extraction, and specifically break down the high molecular weight mucilaginous polysaccharide component to reduce viscosity. In addition, it was surprisingly found adding an amylase in Step (5) was effective to further reduce molecular weight of that polysaccharide component sufficiently to enhance purification of protein during UF downstream.

In Step (5), the use of enzymes after Step (4) further reduces the size of the polysaccharides (now broken down somewhat) to a size that is the same as or less than the size of the soluble leaf proteins. In this way, the later step of filtration (e.g., ultrafiltration and diafiltration) is effective to purify the leaf protein.

Another difference from the first method is that this second method is that the aqueous solution is adjusted to alkaline conditions as noted above. This enhances protein solubility.

Also, unlike the first method, there is no depth filtration after centrifugation. In the first method, the inventors found that low protein yield was at least partly the result of the depth filtration step. This reduced proteins that bind with the filtering medium and are thereby lost. Eliminating the depth filtration also preserves polyphenols as well as beta carotene, and other desired components, in the final product which likely would be removed or diminished by depth filtration.

Like the first method embodiment, the second method may include the additional Step 1a), before or during step 1), which entails reducing pH in buffer solution to an acidic or slightly acidic condition, and prior to step 2) setting pH of buffer solution to a neutral or generally neutral condition. This would further optimize the initial extraction solution pH. If proteolysis becomes an issue, one option is to add an initial low pH step to inactivate proteases prior to alkaline extraction of the proteins. The details of this optional step are describe above in connection with the first method embodiment.

In addition, like the first method embodiment, the second method may include the additional Step 1b), before step 1), conducting a pretreatment step to increase purity and/or yield. The details of this optional step are described above in connection with the first method embodiment.

Like the first method embodiment, the second method may include the additional step, briefly heating the buffer solution to precipitate and facilitate removal of non-protein leaf components. The details of this optional step are described above in connection with the first method embodiment.

Like the first method embodiment, the second method may include the additional step, of precipitating without denaturing soluble leaf proteins by conducting an isoelectric point precipitation on the buffer solution containing the solubilized leaf proteins, for up to 40 minutes at a suitable pH for sweet potato leaves, removing any supernatant; and resuspending the precipitated soluble leaf proteins in the buffer solution. The details of this optional step are described above in connection with the first method embodiment.

Further embodiments and variations within the scope of this invention are described in more detail below.

DETAILED DESCRIPTION OF THE PREFERRED EMBODIMENTS

Figure 1:
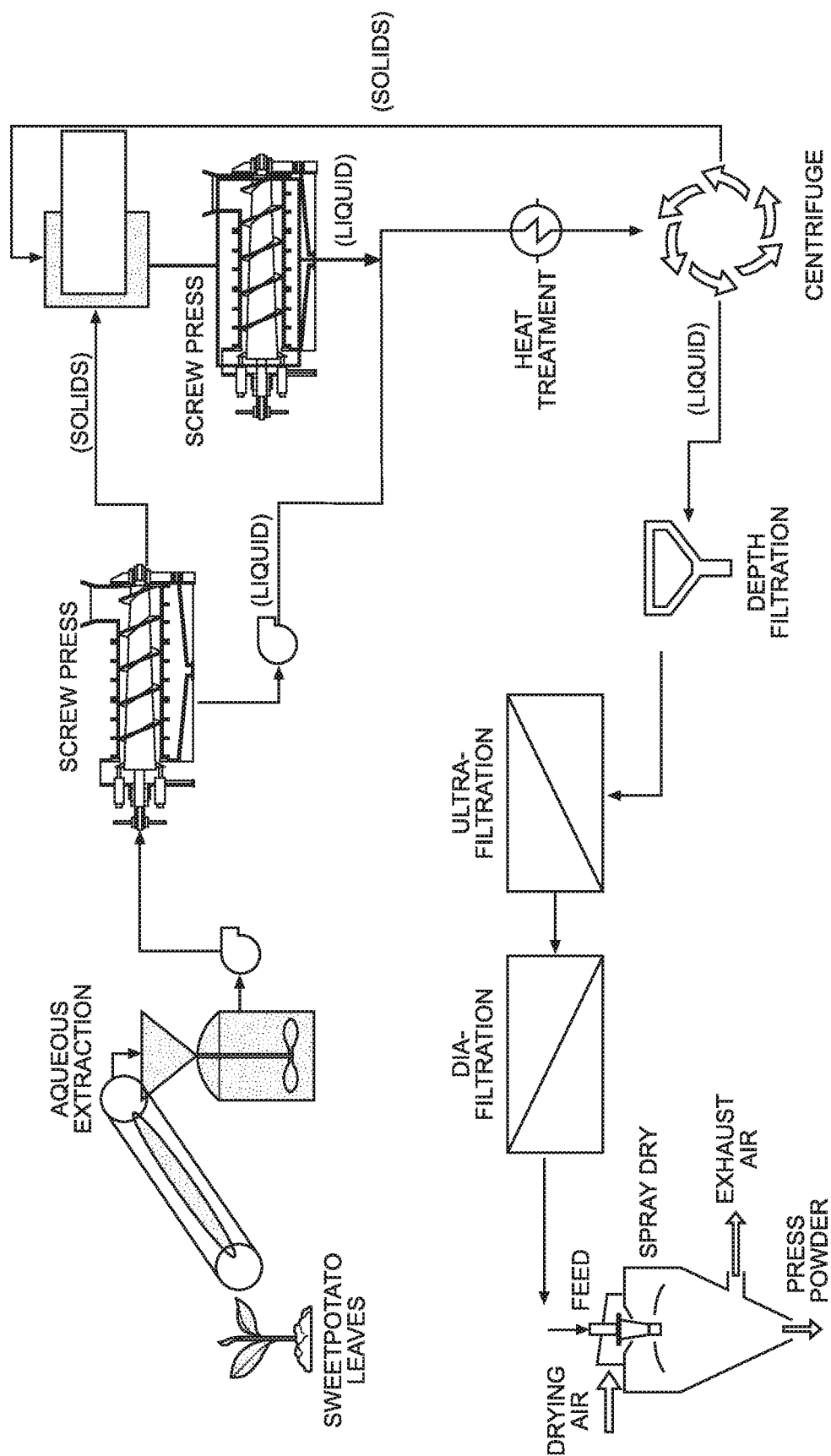
FIG. 1 shows a flow diagram of one preferred process for obtaining sweet potato leaf protein concentrates.

The following description and examples are provided to enable any person skilled in this art to make and use this invention. It is to be understood within the context of the different embodiments and uses of this invention. Besides the specific modifications and options described here, someone skilled in this art would readily understand that the basic novelty defined herein may be applied to other embodiments and applications without departing from the spirit and scope of the present invention. Thus, the present invention is not intended to be limited to the embodiments shown, but is to be accorded the widest scope consistent with the principles and features disclosed herein.

As described above, because of differences in leaf composition and structure compared to other leaves, sweet potato leaves as a source of protein presented unique problems, compared to other crop leaves (e.g., tobacco). For instance, the amount of extractable protein was significantly less. For instance, proteolytic reactions hampered protein yield. Also, extractions from the sweet potato leaves had the unusual problem of clogging (and rendering inoperable or inefficiently operable) filtration equipment, membranes, depth filters, etc. during purification steps downstream. Other obstacles to purity, yield, efficiency, intact proteins, dispersibility, solubility, and the like, came to light and had to be addressed.

As described herein, the inventors developed several different processes that were successful to produce a sweet potato leaf protein concentrate having good protein content (purity) and/or good yield. The problems associated with the sweet potato leaf extraction—and others—were overcome to achieve a protein concentrate that, upon spray drying, was a light colored, pleasant tasting protein-rich powder. Upon examination, the protein concentrate was also found to have additional unexpected properties.

The sweet potato leaf protein concentrate is novel in that it is the first of its kind. No other protein powder concentrate has heretofore been successfully isolated from sweet potato leaves. This proved to be a difficult task, given the issues encountered that are particular to sweet potatoes (both individual problems, and the combination of problems). This invention represents a new composition, a derivative of sweet potato leaf components—a novel concentration of whole leaf, intact (non-denatured), proteins having a high protein content, high purity, yield, high dispersibility and solubility, low viscosity when mixed in liquid, and non-manipulated pleasant taste, odor and other organoleptic qualities. Unique to these compositions, they are free (or trace amounts only) of the high molecular weight mucilage-forming polysaccharide (intact form of it) that interferes with so much of the extraction processes.

The protein concentrate powder can include beneficial polyphenols and other components, which are present in the sweet potato leaf and carefully preserved during extraction (e.g., such as those identified in Fu et al., 2016). In the alternative, polyphenols or other desired ingredients can be added during the process to end up in the final product.

In addition, the protein concentrates can have high levels of rubisco, and are particularly useful as egg white substitutes. Because of the high level and quality of the rubisco, the protein concentrates can also be used quite well in food or beverage products as a gelling agent, a whipping agent, a foaming agent, a thickening agent, an emulsifier, and/or a texturizing agent. A purified rubisco fraction from leaf sources would have even additional value as an egg white replacer in numerous food applications. The protein concentrates have high purity and solubility and/or dispersability so as to be useful in aqueous food systems, such as nutrition shakes, beverages, and bars.

The novel protein concentrates and compositions containing them have advantages over animal proteins with regard to environmental and animal rights issues, as well as advantages over competing plant proteins in nutritional value.

Definitions

By "sweet potato", it is meant any member of the species *Ipomoea batatas* World-wide there are about 6,500 sweet potato varieties including wild accessions, farmer varieties, and breeding lines. All are useful for purposes of this invention. Any known varieties or cultivars would be useful. A non-exhaustive list of many varieties and cultivars can be found at https://en.wikipedia.org/wiki/List of sweet potato cultivars and www.ncsweetpotatoes.com.

The sweet potato (*Ipomoea batatas*) is a dicotyledonous plant that belongs to the bindweed or morning glory family, Convolvulaceae. Of the approximately 50 genera and more than 1,000 species of Convolvulaceae, *I. batatas* is the only crop plant of major importance—many are actually poisonous. The genus *Ipomoea* that contains the sweet potato also includes several garden flowers called morning glories, though that term is not usually extended to *Ipomoea batatas*. Some cultivars of *Ipomoea batatas* are grown as ornamental plants under the name tuberous morning glory, used in a horticultural context.

Botanically, the sweet potato is completely unrelated to the potato (*Solanum tuberosum*) and does not belong to the nightshade family, Solanaceae—although both families belong to the same taxonomic order, the Solanales. Potatoes (*Solanum tuberosum*) are in the Solanaceae family, related to tomatoes, peppers, and eggplant along with deadly nightshade. Sweet potatoes (*Ipomoea batatas*) are in the Convolvulaceae family with flowering morning glory vines.

For purposes of this invention, sweet potato leaves denote the leaves only, and not the stem, flower or tuber or other portion of the plant.

The term "leaf protein" as used in this invention disclosure is intended to refer to all water-soluble proteins contained in plant leaves. It is well known that soluble leaf proteins are found in all known chlorophyll-containing plants. The present invention pertains specifically to soluble leaf proteins.

By "protein concentrate" or "concentrated protein", in the context of this invention, it is meant that there is a high concentration of protein compared to the concentration of soluble leaf protein found in sweet potato leaves in their natural state. For instance, a high concentration may be between over about 21%—about 32% protein of the weight of the total dried down composition. The protein concentrate is unnatural in that it could not be found in nature in such a concentration and purity. This is especially the case with protein obtained from sweet potato leaves, which presents unique challenges to extraction and purification to take the form of a concentrated protein or protein concentrate, alone or in combination with other desired components (e.g., polyphenols).

By "powder" as used in the context of this invention, it is meant that a substance consisting of ground, pulverized, or otherwise finely dispersed solid loose particles. The protein concentrate powder in our invention has a consistency similar to whey concentrate powder. Like most powders, the protein concentrate powder has the distinguishable characteristics of low moisture content (e.g., between 3-10%, and preferably between 5-8% residual moisture), small particle size and even distribution, bulk density, and good flowability (flows freely when shaken or tilted).

By "enzyme" as used in the content of this invention, it is meant an enzyme that catalyzes breakdown or hydrolysis of carbohydrates (especially large carbohydrates and polysaccharides) into simple sugars (e.g, monosaccharides). Our invention contemplates any known enzymes that have this function and capability, and can facilitate breakdown hydrolysis of the high molecular weight carbohydrates and especially the high molecular weight mucilage-forming polysaccharides found in sweet potato leaves. A number of specific carbohydrases are mentioned herein which meet these criteria, but this is by no means an exhaustive list. Someone having skill in this art would know other enzymes that would be effective for the methods described herein, from the description here provided.

By "non-manipulated" as used in the context of this invention, it is meant that the product or compound requires no de-odoring, de-coloring or de-flavoring in the production thereof; and requires no reduction of organoleptic properties in the production thereof; and requires no reduction of astringency in the production thereof. No or minimal chemicals are needed to achieve the desired product or protein concentrate, and no additional engineering of the product or protein concentrate is necessary to achieve the desired purity, color, odor, taste, etc.

By "dispersible" as used in the context of this invention, it is meant the amount of a component (e.g., protein concentrate) that will stay suspended in a mixture with aqueous media, but it will remain separate and will not form a homogeneous solution with aqueous media. For instance, dispersability is determined as the components that remain suspended after one minute holding post high-shear mixing (i.e., whatever has not settled out during that minute). The Protein Dispersibility Index (PDI) is a means of measuring the percent of total protein that disperses in water under standard conditions.

By "soluble" as used in the context of this invention, it is meant the amount of a component (e.g., protein concentrate) that will dissolve in solvent (such as aqueous media) and become part of a homogeneous solution with the aqueous media. For instance, solubility can be determined by how much a component stays in solution after some speed and time of centrifugation.

By "aqueous media" as used in the context of this invention, it is meant a water-based solution, where water is the solvent. Preferably, the liquid is at least 50%, 60%, 70%, 80%, 90%, 95%, 99% or 100% water. Most preferably, the aqueous media is 100% water (e.g., distilled water). Other components of the aqueous media besides water can be present, as long as water is the solvent.

Calculation of crude protein content is accomplished by standard methods using known nitrogen measurements. For example, nitrogen content of a sample (e.g., powder sample) can be quantified via the Dumas method. The standard method for calculating crude protein content is to multiply the % nitrogen by a conversion factor of 6.25. This indicates the purity of crude protein in a sample or batch.

By "denatured" as used in the context of this invention, it is meant that the protein has not lost its quaternary structure, tertiary structure, and/or secondary structure which is present in its native state. The protein has its native conformation, 3D structure, and is folded for proper functioning.

By "disrupted" and "disrupting" as used in the context of this invention, it is meant that the cells, especially cell walls, of the plant materials are broken by external and/or internal forces so that the cell contents, including proteins, are released therefrom.

Protein Concentrate

In a main embodiment, the protein concentrate is concentrated sweet potato leaf protein in dried form. The dried form is preferably powder. Preferably the protein concentrate is dispersible (ranges as described herein) or soluble (ranges as described herein) in aqueous media. The protein concentrate has a high protein content (ranges as described herein), and a high purity (ranges as described herein). The protein concentrate is preferably not denatured, or minimally denatured, or not substantially denatured.

If desired, the protein concentrate powder can contain polyphenols as described herein. The polyphenols are preferably those found naturally in sweet potato leaves, but others can be added to the protein product as desired. If sweet potato leaf polyphenols are desired to be included in the protein concentrate powder, the second method embodiment is the preferred method for production.

In other cases, it may be preferable that sweet potato leaf polyphenols not be included in the protein concentrate powder. For the reasons described herein, it may be preferable that the protein concentrate does not bind with or does not substantially bind with the sweet potato leaf polyphenols. In this case, the first method embodiment is the preferred method for production.

The protein concentrate is preferably non-manipulated, insofar as no reduction of organoleptic properties or astringency is undertaken—no de-odoring, no de-coloring, no de-flavoring additives or process steps are needed in order to create a dried protein concentrate useful for food or beverage products, or general ingestion. This is a very useful advantage over current leaf protein products, which require expensive and time-consuming extractions and special purifications to remove undesirable organoleptic properties (e.g., hexane extractions). The protein concentrate is preferably heat stable and shelf stable.

One of the surprising characteristics of the protein concentrate powder is that it has a high protein content. This is believed to be the first successful recovery of high quality sweet potato leaf protein, having a protein content (or purity) over about 21%, or at least about 24%, or at least about 26%, or at least about 30%, or between 26-30%, or between 26-32%, or up to about 32% by weight of the total protein concentrate. This is in addition to the good qualities of the powder—dispersibility, solubility, and preferably low viscosity in liquid mixture, and having reduced or even the absence of undesirable high molecular weight carbohydrates and polysaccharides.

In one embodiment, the protein concentrate comprises rubisco, of preferable range of weight percent (wt %) as described herein. Approximately half of the soluble protein in plant leaves (such as sweet potato leaves) is made up of "rubisco" (ribulose-1,5-bisphosphate (RUBP) carboxylase/oxygenase or "RuBisCO") (Johal, 1982). Rubisco, which is found in all known green plants, appears to be the most abundant leaf protein, and it may be the most abundant protein on earth (Wikipedia, 2008b). Rubisco is the enzyme which catalyzes both the carboxylation and oxygenation of RUBP in plants, i.e., the key reactions in photosynthesis and photorespiration (Tso, 1990). Rubisco is the primary component of "fraction-1 protein," a term developed by Wildman (1983) to refer to the portion of the soluble leaf protein which can be crystallized out during leaf protein processing.

Rubisco has nutritional value comparable to casein, the milk protein (Wildman, 1983). Studies have shown that rubisco has a significantly higher Protein Efficiency Ratio (PER, i.e., weight gained/protein consumed) than either casein or egg protein (Tso, 2006). Tornatzky (et al., 1996) reported that rubisco appears suitable for kidney dialysis patients and other persons whose bodies do not produce adequate protein, due in part to the fact that rubisco crystals can be washed clean of salts (Tornatzky et al., 1996).

Rubisco also has excellent binding, gelling, foaming, whipping and emulsifying characteristics (Wildman, 1983; Sheen 1991). In addition, rubisco is colorless, tasteless and odorless, which makes it attractive for incorporation into food or industrial products. (Wildman, 1983). Rubisco is relatively stable and can be shipped in crystalline form or produced in a powder (Tornatzky et al., 1996). Given these desirable nutritional and functional properties, rubisco may prove suitable for incorporation into a range of both food and non-food products for such purposes as a nutritional supplement, binding agent or emulsifier. In fact, Wildman (1983) wrote that the functional properties of rubisco are similar to egg albumin or casein.

The remaining half of soluble leaf proteins do not crystallize as readily as fraction-1 proteins. They are sometimes referred to as "fraction-2" proteins (Wildman, 1983), but a term used to describe those proteins which do not crystallize during leaf protein processing. These proteins share, however, many of the same beneficial traits as rubisco. They have a PER and nutritional quality comparable with casein (Tso, 2006; Wildman, 1983). Like rubisco, they are colorless and tasteless (Tso, 2006). Most are also water-soluble (Wildman, 1983). With appropriate extraction methods, fraction-2 proteins could demonstrate the same functional properties as rubisco and have the same commercial applications (Wildman, 1983). Both the so-called "fraction-1" and "fraction-2" proteins are pigment-bound proteins.

Regarding rubisco in particular, the protein concentrate preferably has a rubisco content (or purity) of at least about 21%, or at least about 26%, or up to about 32%.

A certain amount of leaf proteins are non-water soluble. All of the leaf proteins can be included in the protein concentrate, although as a practical matter the protein concentrate will mostly include soluble proteins, including rubisco, since these are the easiest to extract using the methods described below. However, our methods include a novel way to extract the non-soluble proteins as well.

The protein concentrates are useful in compositions, especially in aqueous media due to good dispersibility and/or solubility. The unique properties of the protein concentrates make them suitable for inclusion in food or beverage items—for nutritive value of the protein itself, or as a gelling agent, foaming agent, whipping agent, and the like.

In addition, our methods of production are unique and produce the novel derivative composition protein concentrate powder. One of the methods provides a good yield of the protein concentrate powder.

Methods of Producing

The inventors have developed two novel processes specifically useful for making concentrated sweet potato leaf protein in dried form. The process results in a whole-leaf derived protein powder from sweet potato leaves which is both nutritious and functional in food systems, and which has some or all of the characteristics described above for the protein concentrate.

A biorefinery approach to the use of sweet potato leaves, including both those which are currently waste streams as well as those which may be grown specifically for harvest, can yield a highly nutritious and functional food ingredient for processed food formulators. Simultaneously the process can also yield coproducts of similar high value for the food and food supplement industries, such as antioxidant and colorant compounds. The value increase to growers would be tremendous, and the food industry would benefit from the availability of leaf protein concentrates that can meet all the expressed needs of today's food consumer.

Method #1

As an example of one way by which the process can be carried out, sweet potato leaves are obtained from early plantings, supplemented by leaves picked at maturity of tubers harvested the previous season and held frozen (−20 C) in sealed bags. (Any findings based on this testing can later be verified using mature leaves picked fresh from the same farm at time of tuber harvest).

The main steps can be characterized as:

i) simultaneously disrupting the cell walls of plant leaves and contacting sweet potato leaf soluble proteins (both rubisco and non-rubisco proteins) released from the disrupted plant leaves with a buffer solution;

ii) removing from the buffer solution produced in step (a) substantially all cellulosic material to produce a buffer solution containing plant chloroplast material and the soluble leaf proteins, (preferably under conditions so as to minimize non-protein components present in the buffer solution and minimize breakdown of non-protein material into the buffer solution) and wherein the soluble leaf proteins remain solubilized in the buffer solution;

iii) removing from the buffer solution produced in step (b) at least 60%, or at least 70%, or at least 80%, or at least 90% or at least 95%, or at last 99%, or substantially all of the plant chloroplast material to produce a buffer solution containing the soluble leaf proteins, which proteins remain solubilized therein;

iv) drying down the solubilized soluble leaf proteins from the buffer solution, to produce a protein concentrate in dried form.

The commercial pilot scale process described in FIG. 1 can be simulated at bench scale using a Stephan UM-5 cutter to macerate leaves in buffer (pH 7 phosphate buffer+0.25M potassium metabisulfite), followed by screwpressing using an Super Angel (Tustin Calif.) twin gear juicer 5500. Centrifugation to simulate high speed disc stack processing can be done using a refrigerated Sorvall centrifuge, or for larger runs using the GEA Whisperfuge® located in the NCSU BTEC center. Depth filtration can be carried out using small bench scale cartridges provided by 3M Corp while ultrafiltration utilizes a 10 kDa MWCO membrane on the Alfa Laval M20 unit leased from that company by LeafPro. Some runs can be processed at larger scale using commercial scale pilot plant equipment when large leaf quantities are available (e.g., at time of tuber harvest). At this point depth filtration can use housings and larger cartridges supplied by 3M Corp.

By way of example, in one scaled pilot trial, soluble protein was extracted from fresh sweet potato leaves. The process was run with 600 lbs of fresh sweet potato leaves in one batch. The leaves were first chopped, then mixed with 150 gallons of pH ~7.5 phosphate buffer. The leaves were thus extracted for 1 hour, then fed through an industrial screwpress to remove large, fibrous solids. The juice was then centrifuged in a disc-stack centrifuge, fed through a medical grade depth filtration apparatus to remove small particulates, and then concentrated via tangential flow ultrafiltration with membranes rated at 10 kDa. The resulting concentrated protein-rich liquid was spray-dried into powder form, having a purity of at least about 26% crude protein, up to about 28%.

In one preferred embodiment of this method, proteolysis is minimized or even substantially controlled. Minimization of proteolysis can be important to insuring integrity and yield of proteins (Jacobs 2000), as plant proteases are released from natural encapsulation during maceration of the leaves. While sometimes proteolysis can enhance functionalities such as solubility and/or dispersability, or whipping/foaming, it invariably leads to poorer gelling properties and can also result in considerably decreased protein yields during ultrafiltration. This additional step is described in detail below.

Depending on the desired end-use, in one embodiment of this first method embodiment, and the resultant protein concentrate, it is advantageous that the protein concentrate product is free, or substantially free, from non-desirable compounds. This is especially true of compounds that interfere with native protein conformation and functionality, or which cause an undesirable color, flavor or odor. For instance, it can be desirable that the protein concentrate be at least substantially free of polyphenols, pigments such as chlorophyll and carotenoids, oxidized lipids, and proteases. Some of these, especially polyphenols, react with amino acids, which changes the nutritional value of proteins. So, while polyphenols are often a desirable component, if they are deemed unnecessary for the end-use of the protein concentrate, our invention contemplates a protein concentrate free or substantially free of them. This embodiment of our process in particular is quite useful to achieve this.

An additional optional step is useful to control interaction of bioactive components of leaves with the protein components, so that (a) when desired, the bioactives can be recovered at good yield and purity as valuable, functional coproducts for commercialization (Zhang 2015); and (b) to insure that recovered proteins will exhibit maximum yield and food functionality (primarily solubility and/or dispersability, upon which other functionalities such as whipping, foaming, gelling, etc. ability depend) by preventing the complexing of proteins with bioactives such as polyphenols (Zhang 2015).

To that end, in another embodiment, one or more additional steps are added to the process to additionally precipitate bioactive coproducts in addition to the protein concentrate. Many of the coproducts may have commercial value of their own. It is preferable to include a means by which to capture the leaf proteins that are less water-soluble proteins, in order to maximize recovery economics of whole leaf protein. Preferably, a biorefinery approach is taken so that extraction of other coproducts, such as (a) polyphenols, which may be used in food products for their antioxidant benefits, (b) cellulosics (for energy production), and (c) colorants (for food uses), can be facilitated while still maximizing protein yields.

Another preferred embodiment is to add an ethanol extraction. Preferably, a preliminary ethanol extraction of the sweet potato leaves is added, prior to protein extraction. This can extend the range of valuable leaf constituents that can be captured (Tenorio 2017). Various bioactive compounds such as polyphenols and beta carotene could be isolated and purified, which also would assist in the downstream purification of proteins. The added value of each additionally captured compound thus lowers the cost of isolation for any individual component, including the protein.

One of the features of the protein concentrate produced by this method, is that the interaction of polyphenols with proteins is minimized or controlled. The protein concentrate may not bind at all, or does not substantially bind, with polyphenols. This process can preferably maximize extraction of both proteins and polyphenol as separate entities for commercialization. Interactions of polyphenols with proteins can have either desirable or undesirable effects. Good solubility as is shown by our product is evidence of little denaturation or protein conformational change (when no proteolysis has been used). On the other hand, alteration of protein conformation, and even protein aggregation, can also under certain circumstances enhance functional quality of proteins in foods. For example, certain studies have shown that proteins and polyphenols can behave in a synergistic manner when complexed together, increasing bioactivity and bioefficacy of polyphenols (Ahmed 2014; Grace 2013; Roopchand 2012, 2013). Other recent research has suggested that formation of protein-polyphenol complexes can result in overall enhanced protein functionality in food systems (Schneider 2016; Schneider 2016).

To exert maximum control over interactions of polyphenols with the protein. a 0.025 molar solution of potassium metabisulfite is used to minimize oxidation of chlorophyll and polyphenols (Edwards 1975). This can prevent a substantial green color/flavor in protein powders concentrated from sweet potato leaves. However, this does not result in capture of any value-added products associated with the polyphenol fraction and it does not remove them from the protein environment. As a further step, unreacted polyphenols and excess metabisulfite can however be removed from the protein downstream by diafiltration (Van 2011).

Metabisulfite can also minimize discoloration of proteins during fractionation. Color development may be due to one or more causes. Phenolic compounds such as chlorogenic acid, which are present in the juice, may be oxidized by polyphenol oxidases to o-quinones which may polymerize to brown colored compounds, or may react with peptides and proteins to produce brown or other colored products (Smith and Johnsen 1948; Pierpoint 1969a,b). Browning may also occur by the Maillard reaction (Ellis 1959). Bisulfite additions are known to reduce both enzymatic and nonenzymatic browning reactions (Schroeter 1966).

An alternative way to the control of polyphenol-protein interactions for our process, is the selective removal of polyphenols from proteins or leaf biomass using ethanol extraction. Ethanol/water mixtures can successfully extract polyphenols from wet plant material (Jankowiak 2014). These compounds, which may interfere with protein fractionation or function, actually have important biofunctional value once they have been extracted, such as antioxidant activity (Chiesa & Gnansounou, 2011; Shahidi & Ambigaipalan, 2015) and may also yield useful food colorants. Therefore, their removal during protein extractions can be part of a separate process stream, potentially producing valuable co-products. For instance, this can be used on the leaf biomass prior to aqueous protein extraction, in order to improve the properties of the subsequently extracted proteins, as well as on the dewatered biomass obtained from the screwpress and centrifugation steps after protein extraction, in order to maximize the capture of useful polyphenol coproducts.

To accomplish this, the initial step is to prepare spray dried protein concentrates by either (a) aqueous extraction+/−added sodium metabisulfite (at pH 7 per FIG. 1) or (b) prior extraction of leaf material with cold ethanol, followed by aqueous extraction of the remaining solids, +/−sodium metabisulfite as above. The latter ethanol extraction would thus occur just prior to the aqueous extraction step shown in FIG. 1. It should be noted that in commercial practice soybeans are typically extracted with hexane (to remove oil) prior to aqueous processing into protein concentrates and concentrates, with little detriment to downstream functionality of the proteins (Lusas and Riaz 1995).

Antioxidant potential of ethanol extract of leaves can be assessed, for potential production of leaf protein coproducts. Ethanol extracts can be evaluated. for DPPH (α,α-diphenyl-β-picrylhydrazyl) activity (Keldare and Singh 2011).

One of the advantages of the protein concentrate produced by this method is that the degree of proteolysis is minimized or controlled. When leaf tissue is disrupted in our process, proteolysis can occur which decreases end-yield, quality of the protein concentrate, and other problems. In a preferred embodiment especially useful to make food-grade product, protease activity can be minimized or even eliminated during extraction of leaf proteins by initially adjusting or shifting the pH of the mixture toward an acid (e.g., acidify the mixture). For instance, this can be done using a food grade acid such as HCl (Dijkstra 2003). Proteins can be precipitated, and although their proteins may be slightly altered as a result, changes to protein solubility and/or dispersability (and other food functional properties) would be minimal once pH is restored to near neutral pH. (Lusas and Riaz 1995).

One example to accomplish this is to prepare spray dried protein concentrates by +/−acidification (to pH 3.5; Tenorio 2016) using food grade HCl, just prior to aqueous extraction at pH 7, per FIG. 1. Functionality of protein powders prepared with this protease-inhibition step can be evaluated after restoration of proteins to near neutral pH by addition of dilute NaOH. Proteolysis can be monitored by SDS-PAGE (sodium dodecyl sulfate polyacrylamide electrophoresis; movement of protein bands through a gel under an electrical field) of samples to detect degradation of higher molecular weight protein bands, and in certain cases, also by gel filtration chromatography (Stanton, 2004).

Another variation of this method is to add a subsequent alkaline extraction step to residues remaining from the initial aqueous extraction of rubisco and other water-soluble proteins. Alkaline extraction of edible proteins is known (Lusas and Riaz 1995). A large percentage of the total protein in leaves from most sources is effectively water insoluble at neutral pH (Teng and Wang 2011). For example, Lo's aqueous extraction method (Lo 2010; Lo and Fu 2010) yielded 10 g protein from 1 kg fresh tobacco leaf, which means that more than 60% of the water-soluble proteins in the leaf was recovered. However, if water-soluble proteins comprise only 40% of the whole tobacco leaf proteins (Kung and Tsao 1978; Kung and others 1980; Fantozzi and Sensidoni 1983) then the total protein recovery of this method is less than 25%. After the aqueous extraction and screw-pressing steps, most of the proteins actually remain in the pressed or centrifuged biomass (Teng and Wang 2011).

An additional alkaline extraction step can be added to the process, to solubilize and thereby capture most of the protein present in a leaf source in order to enhance the economics of food protein production from that source. For example, adjusting for sweet potato leaves key process parameters—temperature, NaOH concentration, and extraction time—almost all (e.g., 95%) of the total proteins can be extracted from leaf residue that was not extracted in the previous extraction in the process. In addition, the particle size of the leaf material after disruption can be adjusted to maximize extraction.

Adjusting for sweet potato leaves, an alkaline extraction such as is described in Zhang (2014, 2015) can be applied to the screwpress and centrifugate expelled solids of the typical aqueous protein extraction method shown in FIG. 1. Comparison of total TCA-insoluble nitrogen (thus, protein, when multiplied by the appropriate conversion factor; (Mygomya 2014)) contents before and after such extraction, plus liquid volumes used, can enable mass balance calculation of percent protein extracted, which can subsequently be purified and concentrated by centrifugation, depth filtration, ultrafiltration and spray drying. Protein contents of extracts can be measured by the Bradford method and N analysis of the spray dried protein fraction. Conditions of temperature, NaOH concentration and extraction time are manipulated to optimize the process for expelled biomass of sweet potato leaves. A yield of about 1% protein extracted by fresh weight was achieved.

To attempt to increase yield and purity, it was thought to minimize interference of various non-protein cell constituents. The protein-rich juice resulting from the initial leaf extraction has the problem too much unwanted cellular debris, which the inventors ultimately deduced to be a high molecular weight polysaccharide that, when released from the plant cell, formed a thick viscous mucilage. This caused extensive clogging of additional extraction tools and purification tools (e.g., centrifugation, depth filtration, ultrafiltration membranes). These non-protein compounds lowered the final protein content of the dried-down fraction. To minimize this debris, it was attempted to optimize the initial extraction conditions to maximize protein extraction while preventing breakdown of other cellular material to particulates too small to remove. For example, the method can include post-screwpress processing, a preheating step, and adjusting parameters of centrifugation and depth filtration. Ultimately, these mechanical measures were not sufficiently effective to remove the polysaccharide mucilage.

The initial extraction conditions may obviously affect the level of unwanted cellular constituents dispersed into the extraction medium. Thus, in one embodiment of this process, the buffer:leaf ratio, pH, and temperature of the extraction can individually or collectively be modified to (1) increase or at least not decrease total protein solubilized, and (2) minimize particulates remaining after purification steps such as centrifugation and depth filtration downstream. It was noticed during experiments that, unlike leaf protein extraction of tobacco leaves (e.g., Lo 2010; Lo and Fu 2010), sweet potato leaf extraction presented unique problems with overall yield as well as problems with an overload of particulate waste in the centrifugation step.

An additional option to minimize interference of various non-protein cell constituents is to utilize depth filtration. It was found that the use of depth filtration was useful to good flux in the UF/DF, but it interfered with overall protein recovery. greatly enhanced the yield and product quality, by reducing non-protein particulates Most depth filters used in bio-refining processes are made of cellulose fibers and filter aids (e.g., diatomaceous earth, activated charcoal) bound together by a polymeric resin that provides the necessary wet strength and imparts a cationic surface characteristic. It was found that by altering the depth filter properties (charge, surface area, pore size, etc.) this maximized removal of unwanted particulates while also maximizing passage and recovery of the soluble proteins being targeted. This increased protein throughput, reduced non-protein particulate content (increased protein purity), and resulted higher throughput (flux) in downstream ultrafiltration. For instance, a DE type filter rather than a pharmaceutical grade filter may be preferred. In addition, depth filtration conditions can be altered to take advantage of better precipitation of unwanted cellular constituents that may be facilitated by the preheating step (which follows extraction; see FIG. 1). So the combination of pre-heating and optimized depth filtration can be quite advantageous. Most preferred is to utilize all of pre-heating, adjusted depth filtration and adjusted centrifugation to solve this issue with sweet potato leaf extraction.

As an example of this process: Six hundred pounds of fresh sweet potato leaves and vines were harvested and immediately brought to the pilot plant for processing. Leaves were fed onto a conveyor belt, dropped through a TaskMaster Shredder to disrupt leaf structure, and fed into a 500 gal Breedo mixing tank, jacketed for cooling to 40 F. The chopped leaves were then mixed with 150 gallons of buffer at pH 7.4 consisting of 0.05M $K_2PO_4$, 25 mM potassium metabisulfite, and 5 mM EDTA. After one hour, the mixture was pumped through an industrial screwpress (Vincent Corp.). Solids were screened under pressure and separated from the protein rich liquid. The liquid was then pumped through a Clara series 20 disc stack centrifuge at approximately 8000×G Alfa Laval, then through a dead-end (depth) filtration apparatus made by 3M. The resulting clarified liquid was pumped through an ultrafiltration unit from Alfa Laval containing membranes with nominal 5 kDa pore size, and then diafiltered with 1 volume of water to further purify proteins from small molecular weight molecules. The concentrated protein liquid was then spray dried to produce the final protein concentrate powder.

Results/Conclusion: The uniquely pleasant taste of the sweet potato leaf protein concentrate powder contrasted with the dark, grassy color/flavors of powders produced from either alfalfa or tobacco leaves. This is true even though there were no additional steps needed to decolorize/deodorize as required and indicated in many academic papers as well as the method published in U.S. patent publication US20150335043.

Figure 2:
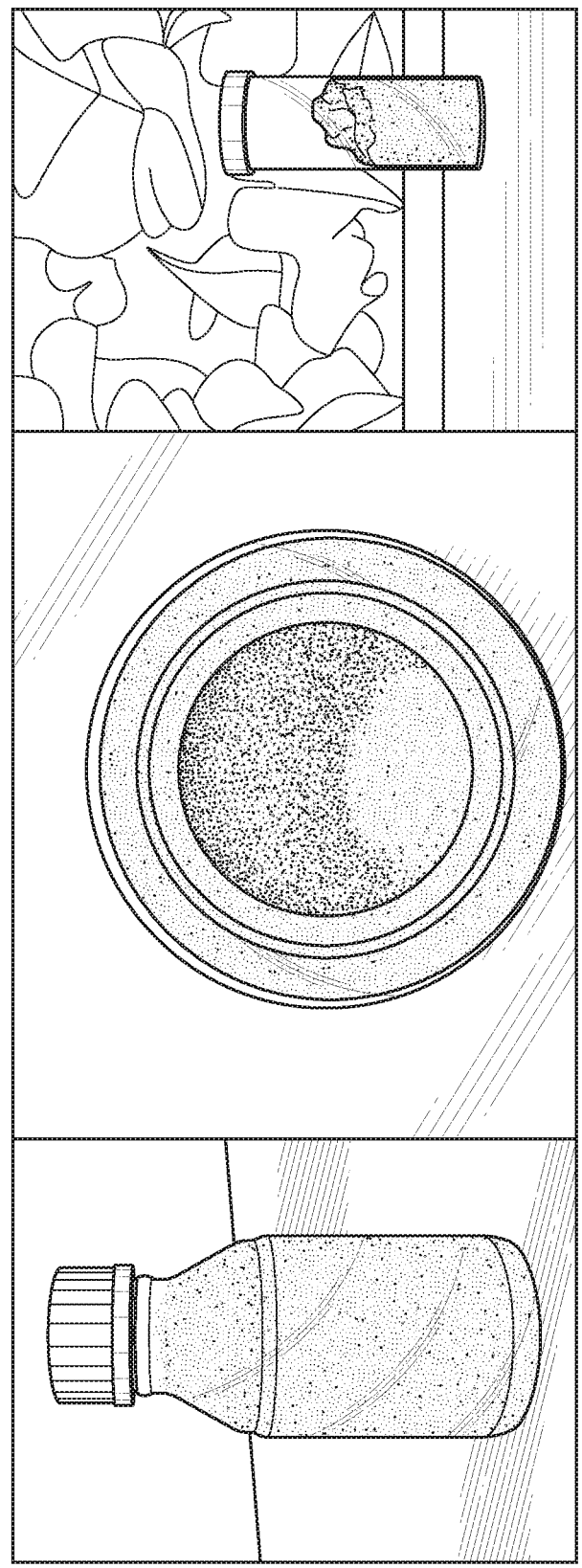
FIG. 2 shows crude protein powder produced from sweet potato leaves. The powder has a light color.
Figure 3:
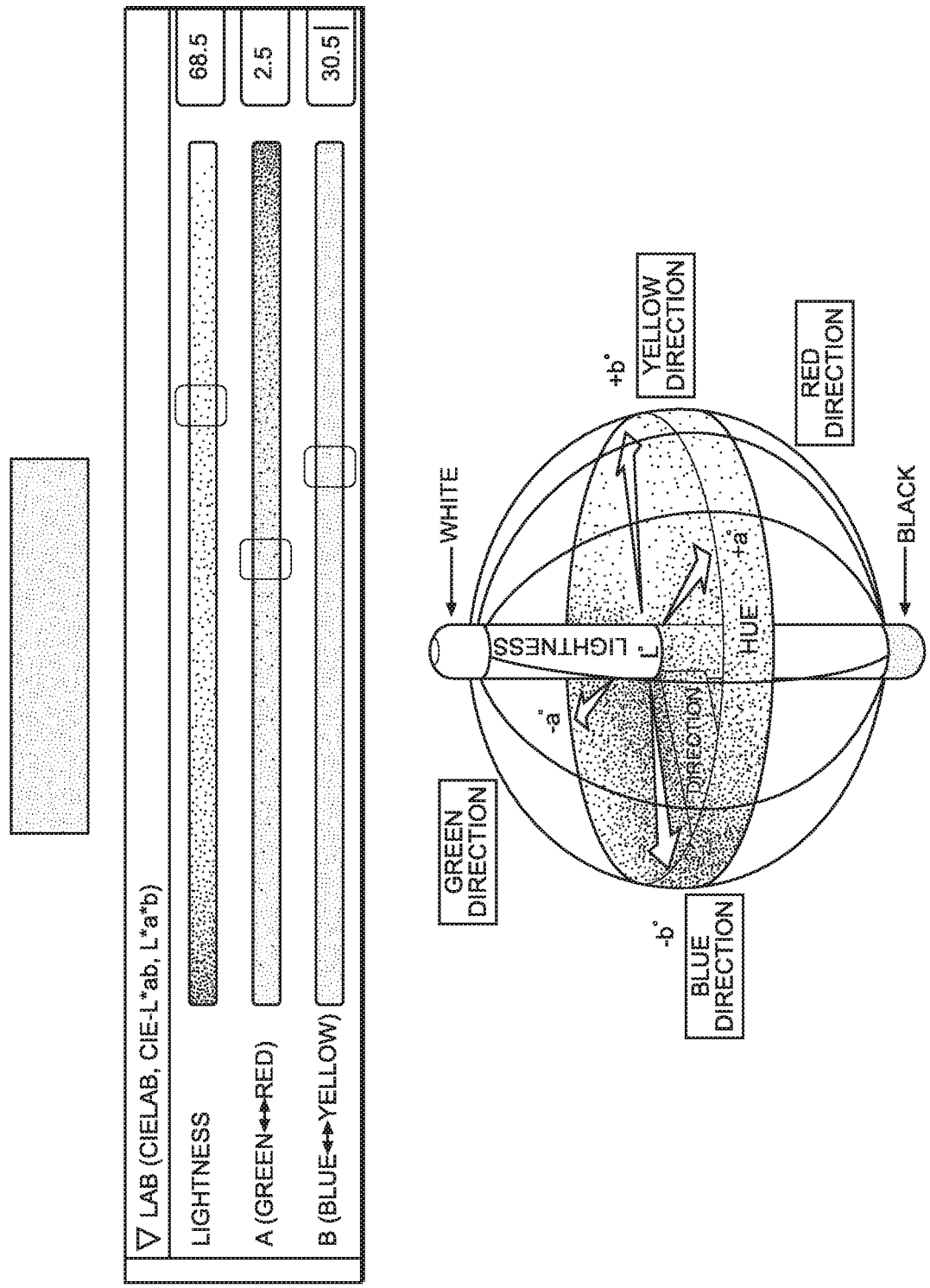
FIG. 3 shows the colorimeter analysis of the protein concentrate powder. The powder was analyzed using a standard colorimeter. At the top of the figure is a rectangular box that shows the actual color of the powder—a light mustard yellow. The color coordinates for this sample are $L^*=68.5$, $a^*=2.5$, and $b^*=30.5$, where L is a measure of the lightness, on a scale from pitch black $L=0$. $a^*=$light assessed in the green-red direction, and $b^*=$light in the yellow-blue direction. The value of 68.5 is a fairly high number, indicating a light color.
Figure 4:
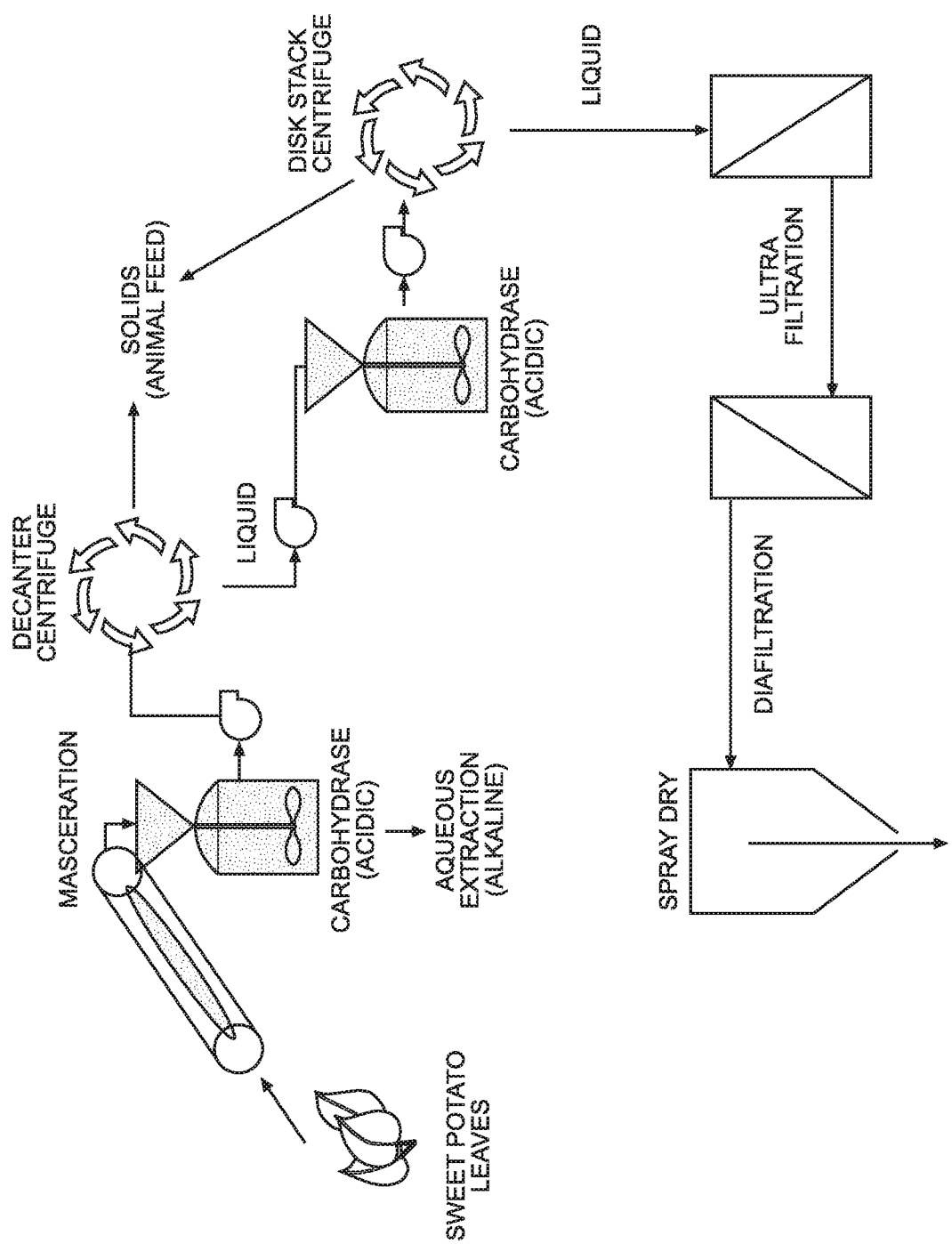
FIG. 4 shows a flow diagram of another preferred process for obtaining sweet potato leaf protein concentrates.

FIG. 2 shows the protein concentrate powder produced by this method, with its light color. Odor, taste, etc. was bland and pleasant, mild and easy to ingest. There were no noticeable unpleasant odors or flavors.

One run gave nitrogen content of 4.343%, or 27.14375% protein using the standard conversion factor of 6.25 (performed 9/24/2017). A second run gave nitrogen content of 4.526%, which is 28.2875% protein (12/01/2017). The yield in both trials was just over 1%.

Three major problems occurred during this experiment. First, the yield in the leaf juice after initial extracting was very low (1% yield). Second, there was significant protein loss during the depth filtration step. Finally, there were problems in getting the sweet potato leaf juice through the centrifuge, because the thick, viscous consistency of the juice and particulates resulted in poor flow rates through the centrifuge.

Method #2

Subsequent to the first production method just described, the inventors developed a second method which was even more effective to produce the sweet potato leaf protein concentrate. The protein content of the end product was much higher in some cases, and the yield was consistently significantly higher as well.

The fresh sweet potato leaves were obtained in a similar fashion as described above for the first method.

The main steps can be characterized as:
1) disrupting the cell walls of plant leaves and contacting soluble sweet potato leaf proteins released from the disrupted plant leaves with an aqueous solution having an acidic pH (that is, less than a pH of 7 and preferably having a pH between 4 and 6), so that soluble leaf proteins are solubilized in the aqueous solution;
2) adding to the aqueous solution at least one enzyme that catalyzes breakdown and/or hydrolysis of carbohydrates, and if needed adjusting the pH to be or remain acidic (preferably between 4 and 6),
3) extracting the aqueous solution at a basic (or alkaline) pH (that is, greater than a pH of 7, and preferably between 10 and 13);

4) removing from the aqueous solution produced in step (3) substantially all cellulosic and starch material to produce an aqueous solution containing plant chloroplast material and the soluble leaf proteins,
5) adding to the aqueous solution of step (4) at least one enzyme that catalyzes breakdown and/or hydrolysis of carbohydrates, and adjusting to an acidic pH (preferably between 4 and 6),
6) filtering (e.g., by ultrafiltration and/or diafiltration) the aqueous solution of step (5),
   wherein throughout steps (1)-(6) the soluble leaf protein remains solubilized in the aqueous solution, and
7) drying down the soluble leaf proteins from the aqueous solution of step (6), to produce a sweet potato leaf protein concentrate in dried form.

In Step 1), preferably the disrupted leaf materials are contacted with the aqueous solution simultaneously, or substantially simultaneously (e.g., as close together in time as possible, preferably within 30 seconds). Steps 1) and 2) can be combined into a single step, or both steps can be carried out simultaneously, or Step 2) can be done immediately after Step 1), or within 5 minutes or within 30 minutes. If the two steps are not combined or simultaneous, the time between Steps 1) and 2) should be minimized as far as possible.

In Step 1), preferably the cells walls of the leaves are disrupted by chopping, milling, grinding or crushing the leaves, pulping, maceration procedures, mechanical pressure, rollers or homogenizing.

Preferably, the process is conducted throughout at a temperature between about 0-25 degrees Celsius.

The enzymes are any that will breakdown and/or catalyze hydrolysis of high molecular weight plant carbohydrates and polysaccharides. One category of enzymes suitable for this is the carbohydrase group. Examples of suitable carbohydrases are arabanase, cellulase, beta-glucanase, hemicellulose, xylanase, and pectinase and amylase (e.g., alpha amylase).

The enzymes used in step 2) and 5) can be the same or different.

In Step 2), the enzymes are preferably one or more of arabanase, cellulase, beta-glucanase, hemicellulose, xylanase, and pectinase. Amylase is also an option, or any enzyme that functions as described above for the purposes of this process.

In Step 5), the enzymes are preferably one or more of beta-glucanase, and amylase (e.g., alpha amylase). It was found that amylase gave unexpectedly good results in protein content and yield. However, any of arabanase, cellulase, beta-glucanase, hemicellulose, xylanase, and pectinase can be used, or any enzyme that functions as described above for the purposes of this process.

Preferably, the process includes the further step of purification of the aqueous solution to precipitate rubisco.

Preferably, in Step 7) the drying down is done by spray drying, vacuum drying, or freeze drying.

This embodiment of the process of producing sweet potato leaf protein concentrate has a good protein content of between about 21%—and 32% by weight, and a yield of at least about 7%, or about 8%, or about 10%, and preferably 12%, based on weight of dry leaf extracted.

Preferably, sweet potato leaf polyphenols are not extracted out, and bind to the leaf proteins. For instance, polyphenols can include one or more of hydrobenzoic acids, hydroxycinnamic acids, flavonoids, stilbenes, and lignans. In particular, hydroxycinnamic acids could include one or more of di-caffeoylquinic acids, caffeoylquinic acids, quercetin-3-glucoside, p coumaric acid and mixtures thereof.

Any of the other polyphenols described herein can also be included, either as a sweet potato leaf extraction product or added to the product separately at any point in the process. Preferably, the polyphenol content is between about 3-5 mg/g (dry weight) in the protein concentrate powder.

Preferably, other beneficial components include at least one of lutein, beta-carotene, biologically active anthocyanins selected from the group consisting of the acylated cyanidin and peonidin types; and compounds having radical scavenging activity, antimutagenic activity, anticancer, antidiabetes, and/or antibacterial activity.

Preferably, the process produces a dried-down protein product which has a water content of less than 10%, and more preferably between 5-8% residual moisture.

Preferably, the process produces a dried-down protein product which has a rubisco content (or purity) of at least about 21% wt.

Preferably, the process produces a dried-down protein product wherein substantially all of the protein concentrate is not denatured (e.g., no more than about 10% wt or preferably no more than 7% or no more than 5% or no more than 3% or no more than 1% of the protein concentrate is not denatured). Preferably, the process produces a dried-down protein product wherein substantially all of the rubisco is not denatured (e.g., no more than about 10% wt or preferably no more than 7% or no more than 5% or no more than 3% or no more than 1% wt of the rubisco is not denatured).

As an example of the process of Method #2:

Step A: Set-up and Acid/Enzyme Extracting: A vertical-cutting machine, with a circulating water jacket of ~40-45 degrees Celsius, is filled with frozen sweet potato leaf (SPL) followed by a volume of liquid equal to twice the mass of frozen SPL. The 43 degree Celsius liquid addition is comprised of: ~5.5 pH DI water, and 1% enzyme (L-Viscozyme) volume per volume of liquid+SPL (SPL density is assumed 1 g/ml). A 3-hour acidic enzyme extraction of SPL is begun with a 3 minute chop at 1,000 rpm, with 30 second chopping sets following every 15 minutes of extracting. The end of three hours has a 3-minute, 1,000 rpm chop, with 8N NaOH added at the completion of minute 1 of the 3-minute chop, thus marking the transition to Step B, "Alkaline Extracting".

Step B: Alkaline Extracting: The last action in Step A, addition of 8N NaOH within a chopping interval, is done with the goal of achieving pH 11 to 12. This pH is held for a 1 hour duration, with a 30 second chopping set every 15 minute interval of time, except for the end of hour chopping. The end of the alkaline extracting hour chopping duration is 3 minutes at 1,000 rpm.

Step C: Treatment Preparation: Resulting extract of Step B is centrifuged at 5,000×G for 15 minutes at air temperature. The supernatant is acidified with 1M HCl to pH ~5.25, followed by L-Viscozyme enzyme added to 1% v/v. The supernatant is split into 3 aliquots by using three separate erlenmeyer flasks as holding vessels. The first erlenmeyer flask is a control, the second erlenmeyer flask has amylase powder (4% amylase ingredient, BSG brand) added at 1.5% amylase powder mass per mass of supernatant, the third erlenmeyer flask has polysorbate 60 (ADM Arkady brand) added at 1 ml per 100 ml supernatant. Treatments, with parafilmed lids, are all put on a stir-bar hotplate for 15 minutes for stirring+heating to ~40 degrees Celsius, before moving on to incubating 3 hours in a circulating water bath.

Step D: Post Incubation: The three incubated treatments have 8N NaOH added until slightly alkaline (pH 8-9). These are centrifuged 15 minutes, 5,000×G at ambient temperature. Supernatant goes on to Step E-UF/DF.

Step E: Ultrafiltration/Diafiltration (UF/DF): Six 10,000 MWCO centrifugal concentrators ("UF/DF tubes"), with Sartorius "Hydrosart" membrane, are each filled to 12.5 ml with a supernatant produced from step D. Two UF/DF tubes each are dedicated to holding any one treatment of the three supernatants of step D. A total of four UF/DF runs are performed (1.5, 1, 1, and 0.5 hour duration respectively) at 5,000×G. DI water is used to replace filtrate volume in DF. All filtrates produced are collected, as well as the retentates of the last UF/DF run. Retentate is collected by pipetting in and out the liquid to incorporate sediment, followed by light membrane scraping with a spatula.

Step F: Oven Drying: Filtrates and retentates, and select samples taken during the procedure are dried in a forced draft oven for quantifying total solids and total nitrogen by Dumas method.

Details on incubation treatments: Treatment 1 is a control, so no modification follows. Treatment 2 is amylase powder addition to the concentration specified in Step C. The 4% amylase powder used is BSG brand, with 96% dextrose (inactive ingredient). Treatment 3 is polysorbate 60 addition to the concentration specified in Step C. The polysorbate 60 brand used is ADM Arkady.

TABLE 1

Protein content and yield:

| Sample | Starting Solids (G) | End Solids (G) | % Yield (5% moisture) | % Protein Purity |
|---|---|---|---|---|
| Sample Run A | | | | |
| 5,000 MWCO 1 Hour | 18.98 | 1.68 | 9.27 | 21.81 |
| 10,000 MWCO 1 Hour | | 1.59 | 8.80 | 22.88 |
| 5,000 MWCO 2 Hour | 18.30 | 1.78 | 10.23 | 26.19 |
| 10,000 MWCO 2 Hour | | 1.85 | 10.62 | 24.69 |
| 5,000 MWCO 4 Hour | 20.06 | 2.32 | 12.16 | 22.94 |
| 10,000 MWCO 4 Hour | | 2.07 | 10.81 | 22.88 |
| Sample Run B | | | | |
| 5,000 MWCO 1 Hour | 19.61 | 1.95 | 10.44 | 23.31 |
| 10,000 MWCO 1 Hour | | 2.09 | 11.17 | 26.13 |
| 5,000 MWCO 2 Hour | 18.25 | 1.65 | 9.49 | 22.00 |
| 10,000 MWCO 2 Hour | | 1.85 | 10.65 | 24.06 |
| 5,000 MWCO 4 Hour | 27.20 | 2.27 | 8.77 | 20.19 |
| 10,000 MWCO 4 Hour | | 2.73 | 10.55 | 22.75 |
| Sample Run C | | | | |
| 5,000 MWCO 0 Hour | 18.98 | 1.68 | 9.27 | 21.81 |
| 10,000 MWCO 0 Hour | | 1.59 | 8.80 | 22.88 |
| 5,000 MWCO 1 Hour | 18.30 | 1.78 | 10.23 | 26.19 |
| 10,000 MWCO 1 Hour | | 1.85 | 10.62 | 24.69 |
| 5,000 MWCO 4 Hour | 20.06 | 2.32 | 12.16 | 22.94 |
| 10,000 MWCO 4 Hour | | 2.07 | 10.81 | 22.88 |
| Control | 17.18 | 1.41 | 8.60 | 30.81 |
| Alpha-Amylase | 18.83 | 1.32 | 7.37 | 32.38 |
| Polysorbate 60 | 19.03 | 2.22 | 12.264 | 20.69 |

In Table 1, the first column is dry weight of leaves extracted. The second column is dry weight of retained final product (UF/DF retentate). The third data column is the calculated yield of spray dried powder, having a 5% moisture content (common for powders). The fourth column is the percent protein content of the final powder. MWCO mean the molecular weight cut off for the pore size indicated, of the filtration membrane.

In Sample Runs A and B, the process was carried out using a cocktail of enzymes (e.g., such as are found in the viscozyme mix) for both enzyme treatments. In Sample Run C, the control is viscozyme in both enzyme treatments, and the "alpha-amylase" run added alpha-amylase in the second of the enzyme treatments. In both treatments, the protein content results were good, although the addition of the amylase improved it to a surprisingly high level.

In all the runs, the % yield of powder was within a range of 7%-12%, and the protein content (purity) was within a range of 21%-32%. The addition of amylase in particular increased protein content significantly, which was a surprise outcome. Both protein content and yield were considered good; the yield in particular was surprisingly consistently strong.

Viscosity of the extraction was tested mid-stream in this process. Using standard visometry equipment, we evaluated a test sample before the enzyme (e.g., Viscozyme) was added, and another test sample after it was added. Using test samples at about 6.5% solids concentration, the test was conducted at room temperature and 120 sec-1 shear rate. We found an extreme difference in the viscosity of the two samples, which we concluded was evidence that addition of the enzyme treatment was effective to breakdown the large polysaccharide causing the mucilaginous build-up in the extract. The results were as follows.

Control (no enzyme treatment): 103.6 cps
Added enzyme treatment: 19.3 cps

Techniques and Options Suitable for both Method #1 and Method #2

As would be understood by someone skilled in this art, some of the steps and details and options described for Method #1 are applicable as options for Method #2, as long as they are not contrasting or inhibitory to the basic steps of Method #2.

It was determined that a brief heat treatment step can precipitate (and facilitate removal of) cell constituents other than the desired, targeted soluble protein fraction. The equipment can be small scale or large scale (e.g., Micro-Thermics tube/tube pilot heat exchanger system or large plate heat exchanger handling multiple gallons per minute), as long as the heating step is brief (e.g., 45 seconds) and not too hot (e.g., 53 C). (Knuckles 1980; Wildman 1983, Eakins 1978; Edwards 1975; De Fremerery 1973 Lamsal 2003). The heating step can be optimized for sweet potato leaf extracts.

Another way to minimize interference of various non-protein cell constituents during the process is to optimize centrifugation time and force. For example, centrifugation conditions can be altered to take advantage of better precipitation of unwanted cellular constituents that may be facilitated by the pre-heating step (which follows extraction; see FIG. 1). So the combination of pre-heating and optimized centrifugation can be quite advantageous.

Both methods may include the additional step, before or during step 1), which entails reducing pH in buffer solution to an acidic or slightly acidic condition, and prior to step 2) setting pH of buffer solution to a neutral or generally neutral condition. This would further optimize the initial extraction solution pH. If proteolysis becomes an issue, one option is to add an initial low pH step to inactivate proteases prior to alkaline extraction of the proteins.

Both methods may include the additional step of precipitating without denaturing soluble leaf proteins by conducting an isoelectric point precipitation on the buffer solution containing the solubilized leaf proteins, for up to 40 minutes at a suitable pH for sweet potato leaves, removing any supernatant; and resuspending the precipitated soluble leaf proteins in the buffer solution.

In both methods, it is preferred no de-odoring, de-coloring or de-flavoring techniques be used. Preferably, no techniques for reduction of organoleptic properties are used. Preferably, no techniques for reduction of astringency are used. In both methods, there is no manipulation of the leaf protein needed to remove or reduce any compounds that cause unwanted color, taste, odor, astringency or other organoleptic properties. This is beneficial since no extra steps or chemicals are needed in the process, and the resultant protein concentrate is more natural, in its native state and otherwise un-manipulated. Preferably, the protein concentrate has a desirable taste profile and/or odor profile, using standard tests for these profiles.

Both methods produce a protein concentrate that is shelf-stable at room temperature for at least 3 months in the absence of stabilizers or additives for maintaining the product in solution and/or dispersion.

In a further step, prior to disruption of the leaves, the fresh leaves can be stored long-term after they are harvested. This gives the advantages of being able to harvest all year long (not limited to when the process will be scheduled to occur). Storage options to keep freshness and protein levels intact include drying, ensiling, or freezing the harvested leaf for later processing.

Regarding rubisco extraction, it is preferred that after the initial whole leaf protein extraction is completed, rubisco can then be extracted with maximum yield and purity. Preferably, at least one membrane is used that will retaining rubisco at 100 kDA. Preferably, purity is increased by using diafiltration volumes appropriate to achieve egg white functionality in the retained rubisco-rich fraction.

The invention will now be illustrated by the following, non-limiting examples.

Measurements & Instrumentation

Yields of protein throughout processing steps are monitored primarily by assessing the protein content as a ratio of both the total weight or volume, or as a ratio of the total solids (dry weight). Thus moisture (and the reciprocal, solids) content, plus accurate measurement of protein (soluble or total) content, are needed.

Solubility of proteins, or at the least, ease of dispersability of proteins in an aqueous mixture, is key to all food functionalities, such as whipping/foaming/gelling etc. The protein concentrate that includes mostly whole leaf protein (versus mostly purified rubisco), finds greatest usage in beverage/shakes/bars or similar products, and therefore solubility and dispersability alone should suffice as indicators of food functionality. With respect to rubisco, other functionality measurements are also useful. Color and taste are important to all applications of food proteins, since lighter color and blander flavor permits greater flexibility of applications.

To determine protein content of dry powder: Nitrogen content of the dry powder was analyzed using a modified Dumas methodology (see http://www.elementaramericas.com/products/organic-elemental-analysis/rapid-micro-n-cube.html for exact instrument and accompanying method).

Moisture (Water) Content: The standard oven drying method is used (AOAC 2006).

Color Measurement: Powder or paste samples are placed in transparent petri dishes and the modified Hunter color values (L*, a*, b*) are measured by reflectance spectrometry using a Minolta CR-300 colorimeter (Konica-Minota Corp, Ramsey N.J.).

Protein Content: Soluble protein contents (protein content of a solution) are measured by the Bradford (1976) method; also see Jones (1989). HPLC-GFC (Stanton 2004) is also used selectively for protein analysis. For solid or non-soluble protein analysis only, nitrogen content is analyzed (Dumas method: Simonne and others 1997) using an Rapid-N-Exceed model nitrogen analyzer, subtracting out the TCA soluble (non-protein) component by N analysis of the supernatant following TCA (10%) precipitation of proteins (Ecoliwiki 2017).

Protein powder (spray dried) solubility and dispersability: The basic difference between these two tests lies in the method of preparing the sample in aqueous suspension, since both ultimately rely on the above Dumas N measurement of protein. Solubility (protein solubility index; PSI) of a protein powder is measured as the protein content (nitrogen, N; protein=N×conversion factor) remaining in solution after slow stirring for two hours, whereas protein dispersability (protein dispersability index, PDI) measures the protein remaining in solution after 10 min of high speed mixing. In both cases the solutions are centrifuged at 3000×G for 5 min and protein is measured in the supernatant and compared as a percentage to the total protein content (based on analysis of the dry powder) of the mixture (Batal 2000). For most uses of the protein concentrates, the PDI is more important than PSI since high shear is typical of the preparation method for these foods (shakes, bars etc.).

Solubility and dispersability were tested based on total solid content and also based on protein content. The tests were conducted by dispersing 1% dry powder into water at room temperature; then adjusted with 0.1N HCl or NaOH solution to pH 6, 7, or 8. The solubility test was 2 hours stirring followed by centrifugation at 6000×G for 10 min prior to measurement of solids/protein remaining in solution. The dispersability test was 10 min at high speed shear with no vortex, settling for 1 min and sampling of liquid to measure solids/protein remaining in solution.

For solids content, data was produced based on solids contents of the powder that were solubilized and dispersed in water (rather than total protein percentage solubilized/dispersed).

Data based on solids: solubility/dispersion:

|  | pH 6 | pH 7 | pH 8 |
| --- | --- | --- | --- |
| Solubility | 89% | 91% | 89% |
| Dispersability | 92% | 94% | 94% |

For total protein content, data was produced based on total protein percentage solubilized/dispersed of the powder were solubilized and dispersed in water.

Data based on protein content: solubility/dispersion:

|  | pH 6 | pH 7 | pH 8 |
| --- | --- | --- | --- |
| Solubility | 79% | 81% | 75% |
| Dispersability | 91% | 94% | 87% |

Based on these data, it was concluded that solubility and dispersability of the protein concentrate dried down product is excellent.

Viscosity of protein concentrate powder, in aqueous solution: The protein concentrate powders produced by both Method #1 and Method #2 were tested for viscosity when in aqueous solution. We tested using 10% solids concentration in water (based on what would be a reasonable usage level in a beverage). This ratio of powder to water was also chosen because it was deemed that if the powder had included in its composition the high molecular weight mucilage-forming polysaccharide in it, the result of mixing it in the same amount of water would be the formation of a thick and viscous mucilage. The powder was thoroughly dispersed in the water. The test was conducted at room temperature, pH 7, and 120 sec-1 shear rate. Both these powders tested had nearly the same protein content.

Results: Method #1—protein concentrate at 10% solids in water had a viscosity of 845 cps. Method #2—protein concentrate at 10% solids in water had a viscosity of 322 cps.

Proteolysis Assessment by (SDS- or native-) PAGE or Size Exclusion Gel Chromatography: For SDS-PAGE (method: Plundrich 2015), the fully denatured protein samples are loaded onto one end of a polyacrylamide gel and an electrical field applied to the gel. The charge on the protein molecules causes them to migrate through the gel; the speed at which they migrate is determined mostly by the physical size of the molecules and the density of the gel. As a result, smaller proteins reach the bottom of the gel before the larger proteins. By staining the gel with Coomassie dye and comparing the samples to a marker containing known proteins, a visual representation can be obtained of the molecular weight distribution of the proteins in the sample. This is particularly useful for plant protein extracts, as the molecular weight of rubisco is much larger than most other native proteins, and so its relative content can be easily determined. Because rubisco is relatively labile, it is useful to determine whether the molecule is recovered intact. This is achieved by analyzing the samples under native conditions, as well as under denaturing conditions using sodium dodecyl sulfate (SDS). The intact molecule under native conditions and the subunits under both conditions are easily detectable, allowing the extent of degradation to be determined by comparing the two. Molecular weight determinations of the protein extracts can also be performed by gel filtration chromatography (Stanton, 2004). In this approach, a volume sample is loaded onto a size exclusion column and carried along the column by an aqueous mobile phase. The stationary phase is porous, and larger molecules are less likely to enter the pores than smaller ones, reducing the length of their flowpath, and therefore their residence time. The column eluent can be analyzed by UV detection.

Particle Size Analysis: Particle size distribution within a fluid sample can be measured using a Mastersizer 3000 instrument (Malvern Instruments; Westborough Mass.). Methods used can follow that of Yin (2015) and Wagoner and Foegeding (2017).

Taste: For taste evaluation of powders or pastes, tasting with agreement and training on uniform descriptors are initially used. Sensory testing for consumer acceptance can be carried out via internal testing by potential users, such as HerbalLife, and/or by contracted consumer taste panel studies conducted by the Sensory Services Center at NC State University (https://sensory.ncsu.edu/).

REFERENCES

An, Le Van, Bodil E. Frankow-Lindberg, Jan Erik Lindberg. "Effect of Harvesting Interval and Defoliation on Yield and Chemical Composition of Leaves, Stems and Tubers of Sweet Potato (*Ipomoea Batatas* L. (Lam.)) Plant Parts." *Field Crops Research*, vol. 82, no. 1, 2003, pp. 49-58, doi:10.1016/s0378-4290(03)00018-2.

Angelica. Understanding Leaf Membrane Protein Extraction. Food Chemistry 217 (2017) 234-243.

Baldasso C, Barros T, Tessaro I. 2001. Concentration and purification of whey proteins by ultrafiltration. Desalination 278:381-386.

Bals B, Dale BE 2015. Economic comparison of multiple techniques for recovering leaf protein in biomass processing. Biotechnol Bioeng 108(3):530-537.

Barbeau W E, Kinsella J E. 1988. Ribulose bisphosphate carboxylase/oxygenase (rubisco) from green leaves-potential as a food protein. Food Rev. Int. 4(1): 93-127.

Batal A B, Douglas M W, Engram A E, Parsons C M 2000. Protein dispersability index as an indicator of properly processed soybean meal. Poult Sci 79(11):1592-6.

Bradford M M 1976. A rapid and sensitive method for the quantitation of proteins.

Buyel J F, Twyman R M, Fischer R. 2015. Extraction and downstream processing of plant-derived recombinant proteins. Biotechnol. Advances. 33 (6): 902-913.

Eakin, D, Singh P, Kohler G, Knuckles B. 1978. Alfalfa protein fractionation by ultrafiltration. J. Food Sci. 43:544-547.

Edwards, Richard H., Raymon E. Miller, Donald De Fremery, Benny E. Knuckles, E. M. Bickoff, George O. Kohler. "Pilot Plant Production of an Edible White Fraction Leaf Protein Concentrate from Alfalfa." *Journal of Agricultural and Food Chemistry*, vol. 23, no. 4, 1975, pp. 620-626, doi:10.1021/jf60200a046.

Fantozzi P and Sensidoni A 1983. Protein extraction from tobacco leaves—technological, nutritional and agronomical aspects. Qual Plant—Plant Foods Hum Nutr 32:351-368 (1983).

Fu et al., "Antioxidant activities and polyphenols of sweet potato (*Ipomoea batatas* L.) leaves extracted with solvents of various polarities", Food Bioscience 15 (2016), pp. 11-18.

Lamsal B P, Koegel R G, Boettcher M E. 2003. Separation of protein fractions in alfalfa juice: effects of some pre-treatment methods. Transact. ASAE 46(3):715-720.

Lo Y M, Fu H, Machado P A, Hahm T S, Kratochvil R J and Wei C I 2010. Recovery of nicotine-free proteins from tobacco leaves using phosphate buffer system under controlled conditions. Bioresource Technol 101(6):2034-2042.

Martin, Anneke H, Oscar Castellani, Govardus A H de Jong, Lionel Bovetto, Christophe Schmitt. "Comparison of the Functional Properties of RuBisCO Protein Isolate Extracted from Sugar Beet Leaves with Commercial Whey Protein and Soy Protein Isolates." *Journal of the Science of Food and Agriculture*, vol. 99, no. 4, 2018, pp. 1568-1576, doi:10.1002/jsfa.9335.

Sun H, Mu T, Xi L, Zhang M, Chen J. 2003. Sweet potato (*Ipomoea batatas* L.) leaves as nutritional and functional foods. Field Crops Research 82(1) 20:49-58

Teng, Zi, and Qin Wang. "Extraction, Identification and Characterization of the Water-Insoluble Proteins from Tobacco Biomass." *Journal of the Science of Food and Agriculture*, vol. 92, no. 7, 2011, pp. 1368-1374, doi: 10.1002/jsfa.4708.

Tenorio A, Boom R, van der Goot A 2017. Understanding leaf membrane protein extraction. Food Chem. 217:234-243.

Van An L, Frankow-Lindberg B E, Lindberg J E 2003. Effect of harvesting interval and defoliation on yield and chemical composition of leaves, stems and tubers of sweet potato (*Ipomoea batatas* L. (Lam.)) plant parts. 82(1): 49-58

Walter et al., "Laboratory Preparation of a Protein-Xanthophyll Concentrate form Sweet Potato Leaves," J. Agric. Food Chem., Vol 26, No. 5, 1978, pp. 1222-1226.

Wildman, S. (1983). An Alternate Use for Tobacco Agriculture: Proteins for Food Plus a Safer Smoking Material. http://www.wws.princeton.edu/cgi-bin/byteserv.prl/~ota/disk3/1983/8315/831507.PDF.

Zhang C, Sanders J, Xiao T, Bruins M 2015. How does alkali aid protein extraction in green tea leaf residue: a basis for integrated biorefinery of leaves. PLoS ONE 10(7): e0133046.

U.S. Patent Documents

| | | |
|---|---|---|
| US20170238590 | August 2017 | Bansal-Mutalik |
| US20150335043 | November 2015 | De Jong |
| 4,588,691 | May 1986 | Johal |
| 4,400,471 | August 1983 | Johal |
| 4,340,676 | July 1982 | Bourque |
| 4,333,871 | June 1982 | DeJong |
| 4,334,024 | June 1982 | Johal |
| 4,268,632 | May 1981 | Wildman and Kwanyuen |
| 4,666,855 | May 1987 | Yang and Langer |
| 5,369,023 | November 1994 | Nakatani et al. |
| 7,034,128 | Apr. 25, 2006 | Turpen et al. |
| 4,347,324 | Aug. 31, 1982 | Wildman et al. |
| 4,289,147 | Sep. 15, 1981 | Wildman et al. |
| 9,321,806 | Apr. 26, 2016 | Lo et al. |
| 9,458,422 | Oct. 4, 2016 | Lo et al. |
| 9,629,888 | Apr. 27, 2017 | Lo et al. |

What is claimed is:

1. A sweet potato leaf protein concentrate powder which is dispersible and/or soluble in aqueous media, wherein the concentrate powder comprises polyphenols selected from the group consisting of hydroxybenzoic acids, hydroxycinnamic acids, flavonoids, stilbenes, and lignans, and wherein the concentrate powder comprises at least one of
lutein,
beta-carotene,
biologically active anthocyanins selected from the group consisting of the acylated cyanidin and peonidin, and
compounds having radical scavenging activity, antimutagenic activity, anticancer activity, antidiabetes activity, and/or antibacterial activity.

2. The sweet potato leaf protein concentrate powder of claim 1, wherein the hydroxycinnamic acids are selected from the group consisting of di-caffeoylquinic acids, caffeoylquinic acids, quercetin-3-glucoside, p coumaric acid, and mixtures thereof.

3. The sweet potato leaf protein concentrate powder of claim 1, which has a protein content between about 21% and about 32% by weight.

4. The sweet potato leaf protein concentrate powder of claim 1, which has a protein content of at least about 30% by weight.

5. The sweet potato leaf protein concentrate powder of claim 1, wherein when the powder is added to aqueous media to form a mixture of 10% solids, the viscosity of the mixture is between about 300-350 centipoise (cP), when measured at room temperature.

6. The sweet potato leaf protein concentrate powder of claim 1, which does not contain more than a trace amount of any high molecular weight mucilage-forming polysaccharide.

7. The sweet potato leaf protein concentrate powder of claim 1, which is at least 85% soluble in aqueous media.

8. The sweet potato leaf protein concentrate powder of claim 1, which is at least 90% dispersible in aqueous media.

9. A protein supplement for a food or beverage, comprising the sweet potato leaf protein concentrate powder of claim 1.

10. The protein supplement of claim 9, wherein the sweet potato leaf protein concentrate powder has a sweet potato leaf protein content between about 26% and about 32% by weight.

11. The sweet potato leaf protein concentrate powder of claim 1, which does not contain chlorophyl.

12. A process for producing sweet potato leaf protein concentrate in a dried form, comprising the steps of:
1) disrupting the cell walls of plant leaves and contacting sweet potato leaf proteins released from the disrupted plant leaves with an aqueous solution at an acidic pH, so that soluble leaf proteins are solubilized in the aqueous solution (Step 1);
2) adding to the aqueous solution at least one enzyme that catalyzes breakdown of carbohydrates, and adjusting if needed the pH to be or remain acidic (Step 2);
3) adjusting the aqueous solution to a basic pH (Step 3);
4) removing from the aqueous solution produced in Step 3 substantially all cellulosic and starch material to produce an aqueous solution containing plant chloroplast material and the soluble leaf proteins (Step 4);
5) adding to the aqueous solution of Step 4 at least one enzyme that catalyzes breakdown of carbohydrates, and adjusting the pH to be acidic (Step 5);
6) filtering the aqueous solution of Step 5, wherein throughout Steps 1-6 the soluble leaf protein remains solubilized in the aqueous solution (Step 6); and
7) drying down the soluble leaf proteins from the aqueous solution of Step 6, to produce a sweet potato leaf protein concentrate in dried form (Step 7).

13. The process of claim 12, wherein Step 1 and Step 2 are carried out simultaneously, or Step 2 is carried out within 5 minutes of Step 1.

14. The process of claim 12, wherein in Step 2 the at least one enzyme is selected from the group consisting of arabanase, cellulase, beta-glucanase, hemicellulase, xylanase, pectinase, and amylase.

15. The process of claim 12, wherein in Step 5 the at least one enzyme is selected from the group consisting of beta-glucanase and amylase.

16. The process of claim 12, wherein in the sweet potato leaf protein concentrate produced thereby has a protein content of between about 21% and about 32% by weight.

17. The process of claim 12, which produces a yield of protein concentrate of at least 7% based on weight of dry leaf extracted.

\* \* \* \* \*